United States Patent
Withey

(10) Patent No.: US 11,098,304 B2
(45) Date of Patent: Aug. 24, 2021

(54) COMBINATORIAL SETS OF NUCLEIC ACID BARCODES FOR ANALYSIS OF NUCLEIC ACIDS ASSOCIATED WITH SINGLE CELLS

(71) Applicant: ATRECA, INC., Redwood City, CA (US)

(72) Inventor: Gary Withey, San Francisco, CA (US)

(73) Assignee: ATRECA, INC., San Carlos, CA (US)

( * ) Notice: Subject to any disclaimer, the term of this patent is extended or adjusted under 35 U.S.C. 154(b) by 0 days.

(21) Appl. No.: 15/772,723

(22) PCT Filed: Nov. 4, 2016

(86) PCT No.: PCT/US2016/060576
§ 371 (c)(1),
(2) Date: May 1, 2018

(87) PCT Pub. No.: WO2017/079593
PCT Pub. Date: May 11, 2017

(65) Prior Publication Data
US 2018/0320171 A1    Nov. 8, 2018

Related U.S. Application Data

(60) Provisional application No. 62/250,900, filed on Nov. 4, 2015.

(51) Int. Cl.
*C12N 15/10*    (2006.01)
*C12Q 1/6806*   (2018.01)

(52) U.S. Cl.
CPC ..... *C12N 15/1096* (2013.01); *C12N 15/1065* (2013.01); *C12Q 1/6806* (2013.01)

(58) Field of Classification Search
CPC ............ C12N 15/1096; C12N 15/1065; C12Q 1/6806
See application file for complete search history.

(56) References Cited

U.S. PATENT DOCUMENTS

| | | |
|---|---|---|
| 5,962,272 A | 10/1999 | Chenchik et al. |
| 8,632,977 B2 | 1/2014 | Chun |
| 9,249,457 B2 | 2/2016 | Carninci et al. |
| 9,410,173 B2 | 8/2016 | Betts et al. |
| 2012/0010091 A1 | 1/2012 | Linnarson |
| 2015/0111789 A1 | 4/2015 | Betts et al. |
| 2015/0203906 A1 | 7/2015 | Betts et al. |
| 2015/0299784 A1* | 10/2015 | Fan .................. C12Q 1/6874 506/4 |
| 2015/0376609 A1* | 12/2015 | Hindson ............ C40B 20/04 506/4 |
| 2016/0258016 A1 | 9/2016 | Sandberg et al. |

FOREIGN PATENT DOCUMENTS

| | | |
|---|---|---|
| WO | 2007018601 A1 | 2/2007 |
| WO | 2010/117620 A2 | 10/2010 |
| WO | 2011/155833 A2 | 12/2011 |
| WO | 2012/048341 A1 | 4/2012 |
| WO | 2012083225 A2 | 6/2012 |
| WO | 2012/148497 A2 | 11/2012 |
| WO | 2014/071361 A1 | 5/2014 |
| WO | 2014/144495 A1 | 9/2014 |
| WO | 2014/145992 A1 | 9/2014 |
| WO | 2014/201273 A1 | 12/2014 |
| WO | 2014/210353 A2 | 12/2014 |
| WO | 2015/002908 A1 | 1/2015 |
| WO | 2015/031691 A1 | 3/2015 |
| WO | 2015/103339 A1 | 7/2015 |
| WO | 2015/164212 A1 | 10/2015 |
| WO | 2015/173402 A1 | 11/2015 |
| WO | 2016044227 A1 | 3/2016 |
| WO | 2016138490 A1 | 9/2016 |
| WO | 2016/172373 A1 | 10/2016 |
| WO | 2016160844 A2 | 10/2016 |

OTHER PUBLICATIONS

EPO Patent Application No. 16801644.2 Communication dated Mar. 26, 2019.
Abate, R. Lab on a Chip 9 (2009).
DeKosky, BJ, Nat Biotechnol, 31(2), 2013.
International Search Report received in the corresponding PCT Application No. PCT/US2016/060576, dated Apr. 20, 2017.
Klein, A. Cell, 161 , 2015.
Qiu, Fang, et al., 'DNA sequence-based "bar codes" for tracking the origins of expressed sequence tags froma maize cDNA library constructed using multiple mRNA sources', *Plant Physiology, American Society of Plant Physiologies*, vol. 122, No. 2, 2003.
Macosko E.Z., et al., "Highly Parallel Genome-Wide Expression Profiling of Individual Cells Using Nanoliter Droplets", *CELL*, 2015, vol. 161, No. 5, pp. 1202-1214.
Search Report received for Patent Application No. 11201803646Y dated Sep. 4, 2019.

* cited by examiner

*Primary Examiner* — Robert H Havlin
(74) *Attorney, Agent, or Firm* — Kilpatrick Townsend & Stockton LLP

(57) ABSTRACT

Provided herein are methods of identifying the origin of a nucleic acid sample. The methods include forming a reaction mixture comprising a nucleic acid sample comprising nucleic acid molecules from a single cell and a set of barcodes, incorporating the set of barcodes into the nucleic acid molecules of the sample, and identifying the set of barcodes incorporated into the nucleic acid molecules of the single cell thereby identifying the origin of the nucleic acid sample.

40 Claims, 14 Drawing Sheets
Specification includes a Sequence Listing.

COMBINATORIAL SETS OF NUCLEIC ACID BARCODES FOR ANALYSIS OF NUCLEIC ACIDS ASSOCIATED WITH SINGLE CELLS

CROSS REFERENCE TO RELATED APPLICATION

This application is a U.S. National Phase of PCT/US2016/060576, filed Nov. 4, 2016, which claims priority to U.S. Provisional Application 62/250,900, filed Nov. 4, 2015, the contents of each of the above are herein incorporated by reference in the entirety.

BACKGROUND OF THE INVENTION

Genomic and transcriptomic profiling of cell populations is an area of intense and growing interest with considerable implications in the fields of biotechnology and medicine. Recent advances in nucleic acid sequencing technology have enabled profiling studies on a scale that far outpaces the practical throughput of conventional approaches. Early efforts towards single-cell genomic or transcriptomic profiling involved FACS sorting or even hand-picking of individual cells into separate reaction vials, such as the wells of a multi-well microtiter plate, in which the genomic or transcriptomic analytical method of choice can be applied. In this format the separate reactions can be individually manipulated and controlled. It is relatively straightforward, for instance, to ensure that each well contains only a single cell. This is important since the co-sequestration of multiple cells will lead to the convolution of the genomic or transcriptomic profiles of those cells with one another, and disentangling the individual profiles will be difficult or impossible. The disadvantage of these formats are that they are time-, reagent-, and labor-intensive, and for these reasons allow only relatively low-throughput processes. More recent approaches have trended towards the sequestration of cells and the required chemical and molecular reagents in nanoliter- or picoliter-sized containers such as micro- or nano-wells or droplets. These formats allow for vast improvements in terms of time, cost, and throughput with the disadvantage that it is considerably more challenging to control the precise loading of cells and other reaction components into the containers. The components are often assigned to their containers at random, in which case the distribution of the components among the many containers follows a Poisson distribution. In the case of cells, for example, if the system requires that at least 95% of cells be singly-sequestered (in other words, only 5% of containers with a cell are tolerated to contain two or more cells), the conditions must be set so that each container receives, on average, 0.1 cell. In Poisson terms, this is an expected value, or "lambda," of 0.1. In this case, 90.48% of containers will receive no cells, 9.05% of containers will receive a single cell, 0.45% will receive two cells, 0.02% will receive three cells, and a lower percentage will receive four, five, six, etc. Of the containers that receive a cell in this case, 95.1% contain exactly one cell. The inefficiency of such a system is apparent as greater than 90% of all reaction containers lack a cell and are therefore unproductive. The inefficiency is compounded when the intersection of two or more of these Poisson distributions are involved. A common approach to genomic and transcriptomic profiling involves the sequestration of a cell along with a nucleic acid barcode that is then appended to the genes and/or transcripts originating from that cell. The barcode is later used to unambiguously assign each gene or transcript to its cell of origin, thus comprising that cell's genomic or transcriptomic profile. The disambiguation of such a scheme depends not only upon cells being singly-sequestered but also for the same container to receive only a single barcode. The barcode may be a single nucleic acid molecule, but more commonly is delivered via a particle such as a polystyrene bead, the surface of which is functionalized with many copies of an identical nucleic acid barcode. In either case, the random assignment of unique barcodes to reaction containers will follow the same loading statistics as before, namely a Poisson distribution determined by the expected value (lambda). Only containers in which exactly one cell is co-sequestered with exactly one barcode will yield unambiguous genomic or transcriptomic profiles. Multi-cell sequestration with a particular barcode, upon downstream data analysis, will appear as a single genomic or transcriptomic profile that is the union of the individual profiles of the co-sequestered cells. Cases of co-sequestration of multiple cells with multiple barcodes result in yet more complex ambiguity. This ambiguity has adverse implications for all applications involving single-cell genetic or transcriptomic profiling. For example, if the application involves quantitation of a particular clone that is identified by its transcriptomic profile, cases where multiple barcodes are co-sequestered with a cell of that clonal type will give the appearance of multiple cells of that clonal type in the downstream analysis, and so artificially inflate its apparent percentage of the overall population of cells in the sample. For a profiling system of this design that requires that at least 95% of containers receiving a cell and a barcode receive exactly one cell and exactly one barcode, there is a continuum of cell and barcode lambda combinations that give the desired result (note that if a container fails to receive at least one of each, it is unproductive and drops from consideration). One representative combination is a lambda of 0.05 for both cells and barcodes. In this case a container will receive, on average, 0.05 cells and 0.05 barcodes. Of cells and barcodes each, 95.12% of containers will receive zero, 4.76% will receive one, 0.12% will receive two, and a lower percentage will receive three, four, five, etc. Of the containers receiving at least one cell, 97.52% will receive exactly one cell, and similarly for barcodes. Overlaying these two percentages gives 97.52%×97.52%=95.1% of cell-barcode co-sequestration events as exactly one cell and exactly one barcode. In order to achieve this standard, however, greater than 99.76% of containers are unproductive as they will receive no cell, no barcode, or neither. In other terms, fewer than 0.24% of containers will have the opportunity to produce a cell profile. In addition, since fewer than 5% of cells are co-sequestered with a barcode, more than 95% of cells are lost from analysis. This greatly decreases the throughput of the system and is especially detrimental when the cells of interest to be analyzed are rare cells, as this results in loss of 95% of cells from analysis. These pico- and nano-liter-scale methods could realize meaningful improvements in terms of both throughput (i.e., the number of cells that are processed) and sample coverage (i.e., the percentage of the total number of cells in the original sample that are processed) if the percentage of containers that receive a barcode could be increased without sacrificing the fidelity of the barcoding scheme.

For genomic and transcriptomic profiling approaches that use monoclonal "packets" or "sets" of nucleic acid barcodes, such as barcode nucleic acid-functionalized beads, hydrogels loaded with nucleic acid barcodes, or similar barcode delivery methods, the packets of nucleic acid barcodes nearly always exhibit some degree of polyclonality. The extent of polyclonality depends on the method used to create the barcode packet. For example, one method uses beads that are functionalized with a DNA oligo with a universal priming sequence and emulsified with individual barcode molecules that then amplify onto the surface of the beads by PCR. In this scheme, each droplet in the emulsion may contain several beads that all receive the same barcode sequence, but in the ideal case any given droplet would only receive one barcode nucleic acid. If two or more barcode nucleic acids enter a single droplet, any beads produced in that droplet will be polyclonal. Barcode nucleic acid molecules will be assigned to droplets according to a Poisson distribution that can be tuned by changing the barcode concentration. Here again there is a trade-off. Lower concentrations of barcodes will produce beads that have a higher degree of monoclonality, with the downside cost that fewer overall barcoded beads will be produced. Higher concentrations will increase barcoded bead yield where a greater proportion of beads will exhibit higher polyclonality. Polyclonality is built into the design of this method. Another method for packaging nucleic acid barcodes involves combinatorial synthesis. Performed in a 384-well plate, each well contains a large number of particles—in this case, a hydrogel—that is functionalized with a universal DNA oligo primer. Each well also contains a distinct initial barcode sequence that is incorporated into each hydrogel in that well via PCR. The hydrogels are then pooled together and redistributed into another 384-well plate, each well of which contains a distinct secondary barcode sequence that is incorporated into each hydrogel, again by PCR. The resulting library of hydrogels by this method have a diversity of ~150K barcodes, and theoretically should exhibit a high degree of monoclonality. In practice, however, it has been reported that the method yields a non-negligible degree (~8%) of polyclonality (Klein, A. Cell 161 (2015). This polyclonality could arise either from contamination of hydrogels or barcode nucleic acids between wells of the PCR plate at either PCR step, or from contamination of the original barcode nucleic acid library—either initial or secondary barcoding sequence, or both. Whether by design or by contamination, any polyclonality to the library of barcode packets will confound a genomic or transcriptomic profiling system that is designed to assign a single barcode to each cell. A barcoding scheme would benefit from any ability to cope with some degree of polyclonality in the library of barcode packets.

There are some examples of approaches that have been taken to overcome or avoid the inefficiency that arises from Poisson-based distribution of nucleic acid barcodes. A transcriptomic profiling method has been reported that uses hydrogel particles that are loaded with individual barcodes and introduced into the aqueous stream of a droplet device immediately prior to encapsulation in a droplet along with cells (which are randomly loaded according to a Poisson distribution with a lambda of 0.1-0.2). Because the hydrogels are highly conformable, they can be packed into single file in a narrow inlet, and introduced in a highly ordered procession that can be synchronized with the rate of droplet formation. As a result, nearly all droplets receive one hydrogel particle (Abate, R. Lab on a Chip 9 (2009)) with many copies of a unique barcode. However, while such a carefully-tuned experiment can be executed in a highly optimized environment and by expert hands, it remains to be seen whether this approach is sufficiently scalable and robust for widespread use. In addition, the scheme is not robust to polyclonal barcode packets. Other approaches have involved the incorporation of multiple genomic or transcriptomic targets of interest together into single continuous amplicons, as in the case of overlap extension PCR. These approaches rely on tailored universal primer sets to physically link the targets of interest rather than appending a barcode to each target. Since the primer sets are universal and many copies are introduced into every container, the mechanism by which targets are assigned to their cells of origin does not face the disadvantage of a Poisson-driven distribution. However, these approaches are severely limited in the number of potential genes or transcripts that can be targeted from each cell. Most if not all existing methods are presently limited to two (DeKosky, B J, Nat Biotechnol 31(2) (2013)).

BRIEF SUMMARY OF THE INVENTION

Provided herein are methods of identifying the origin of a nucleic acid sample. The methods include forming a reaction mixture comprising a nucleic acid sample comprising nucleic acid molecules from a single cell and a set of barcodes, incorporating the set of barcodes into the nucleic acid molecules of the sample, and identifying the set of barcodes incorporated into the nucleic acid molecules of the single cell thereby identifying the origin of the nucleic acid sample. Also provided are methods of identifying the origin of a nucleic acid sample that include providing a set of 5' and 3' nucleic acid constructs each construct comprising a unique 5' or 3' barcode sequence respectively, providing a nucleic acid sample comprising nucleic acid molecules from a single cell, contacting the nucleic acid sample with the set of 5' and 3' nucleic acid constructs, incorporating into the nucleic acid molecules the 5' and 3' barcode sequences from the 5' and 3' nucleic acid constructs respectively, and identifying the set of 5' and 3' barcode sequences thereby identifying the origin of the nucleic acid sample from the single cell.

Figure 4:
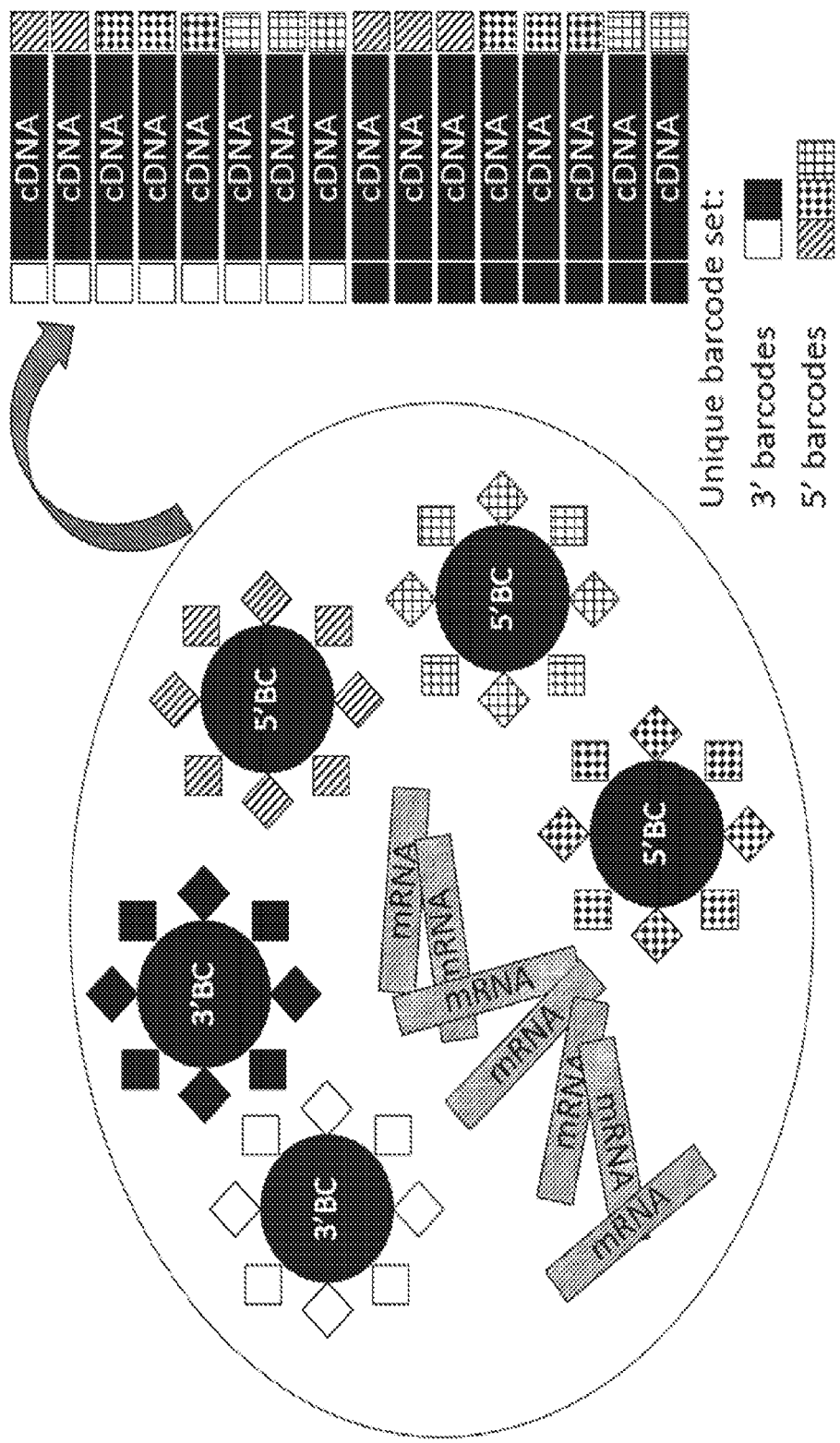

FIG. 4 is a schematic showing two 3' barcoded beads and three 5' barcoded beads are co-encapsulated with a cell. Each 3' barcode pairs with each 5' barcode and vice versa to form a cohesive, unique barcode set that identifies all transcripts as originating from this cell.

Figure 5:
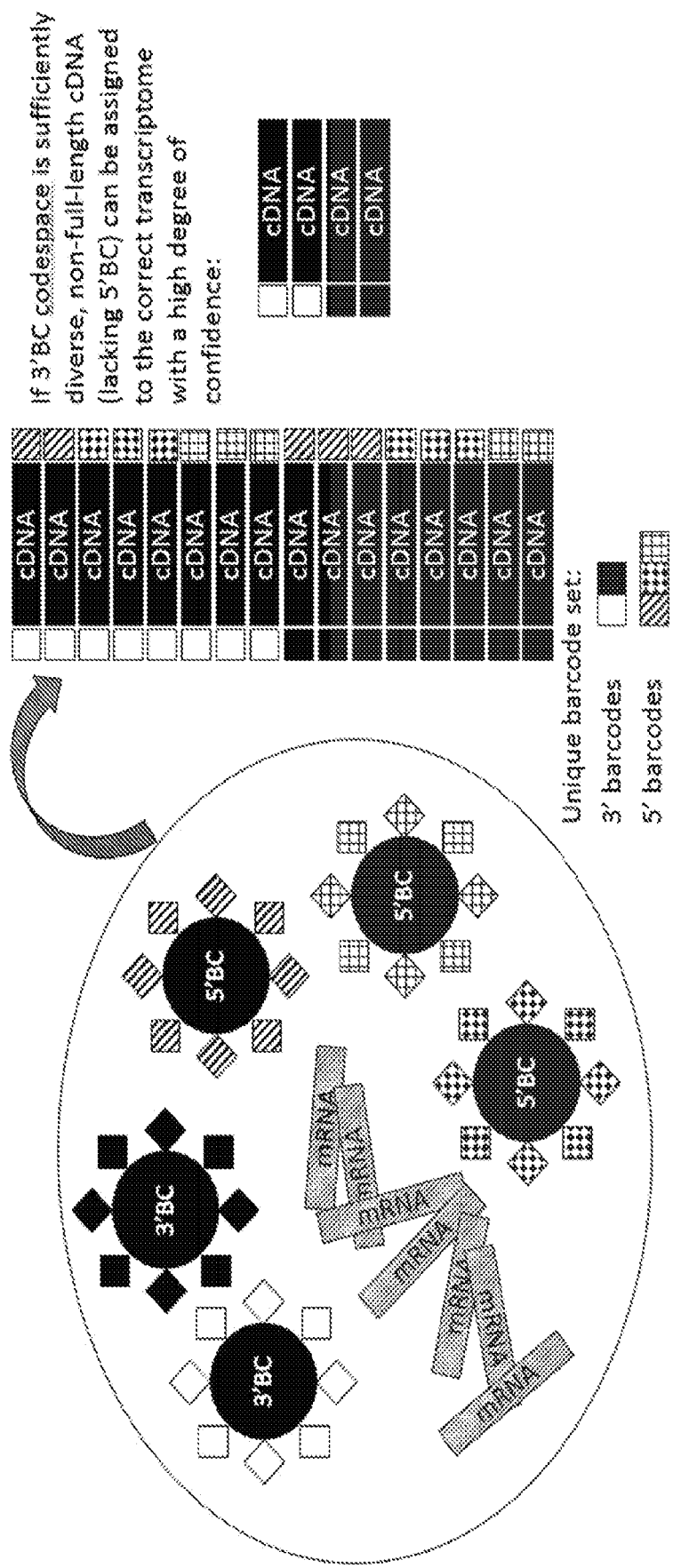

FIG. 5 is a schematic showing that when reverse transcription is prematurely terminated, the cDNA will fail to incorporate a 5' barcode. The library of 3' barcodes can be designed in such a way (in terms of the total number of barcodes) that it becomes extremely unlikely that any one barcode will be co-encapsulated with multiple cells. In this case, the non-full-length barcoded cDNA can be assigned to the proper profile with a high degree of confidence.

Figure 6:
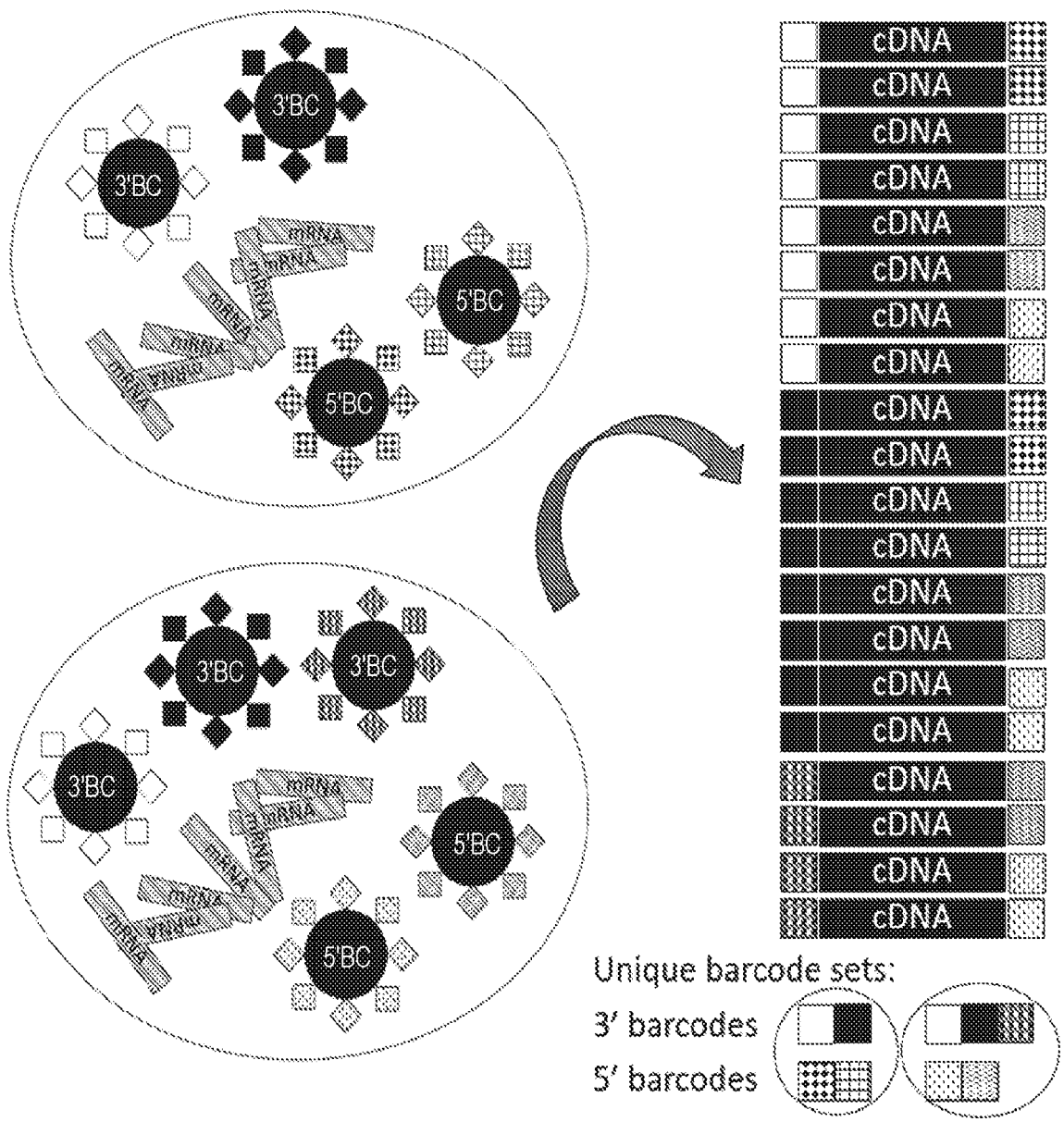

FIG. 6 is a schematic showing that although the same two 3' barcode sequences are co-encapsulated in two different droplets, the two barcode sets are nonetheless distinguishable due to the extra 3' barcode in one droplet. Since this third 3' BC does not pair with the two 5' BC's of the other droplet, the lines that separate the two barcode sets can be drawn unambiguously.

Figure 7:
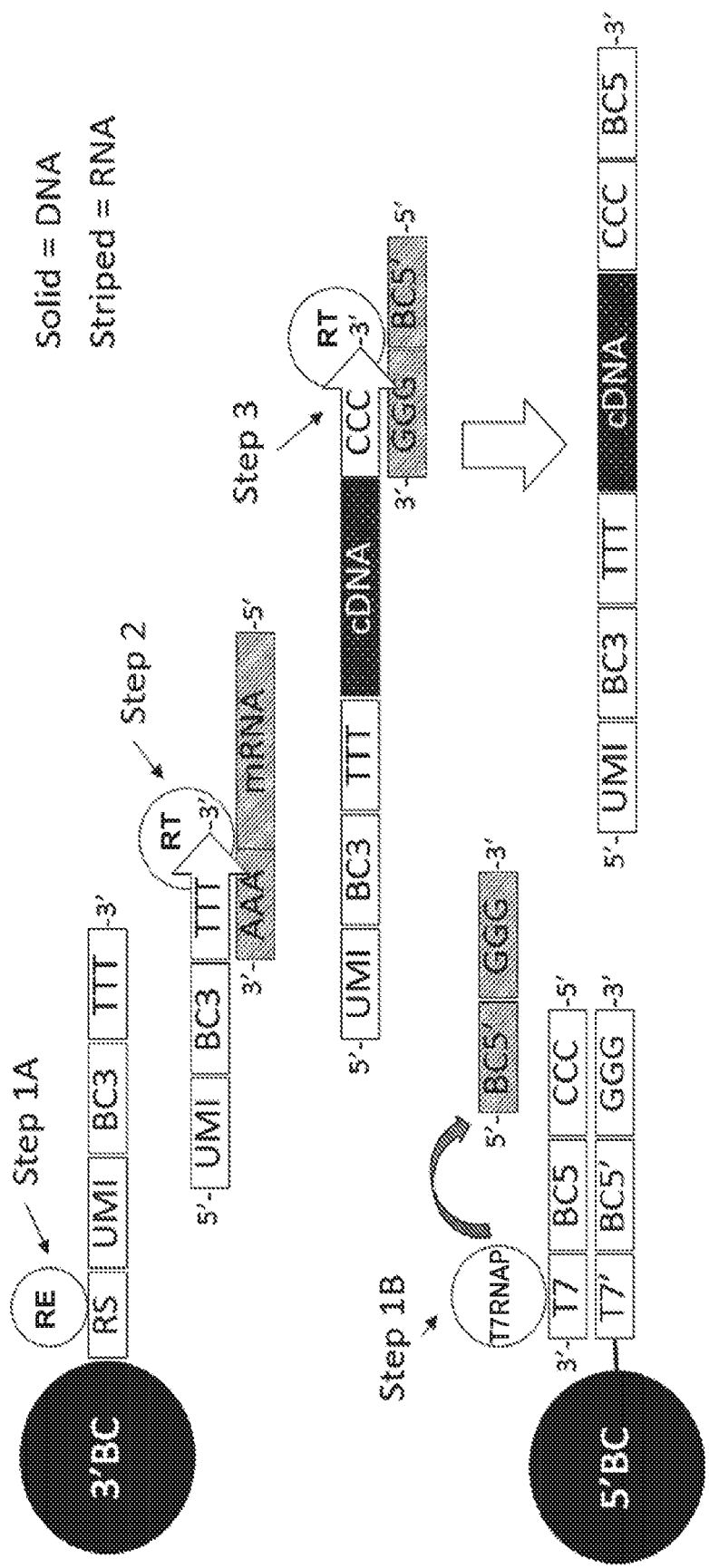

FIG. 7 is a schematic showing the use of a of an exemplary barcode set. Here, the 5' barcode bead set is functionalized with a double-stranded DNA oligo, the hybridized (non-covalently-bound) strand of which comprises a T7 promoter sequence ("T7"), a barcode sequence, and three cytosine residues. Rather than being cleaved from the bead surface by a restriction enzyme, the T7 promoter allows a T7 RNA polymerase to bind and transcribe RNA barcode copies from the DNA oligo template on the bead surface. These RNA barcode copies will terminate at the 3' end with three guanine residues that will enable them to anneal to the 3' end of full-length, 3'-barcoded cDNA. The RT enzyme template-switches to the 5' barcode RNA oligo template and incorporates the 5' barcode into the cDNA.

Figure 8:
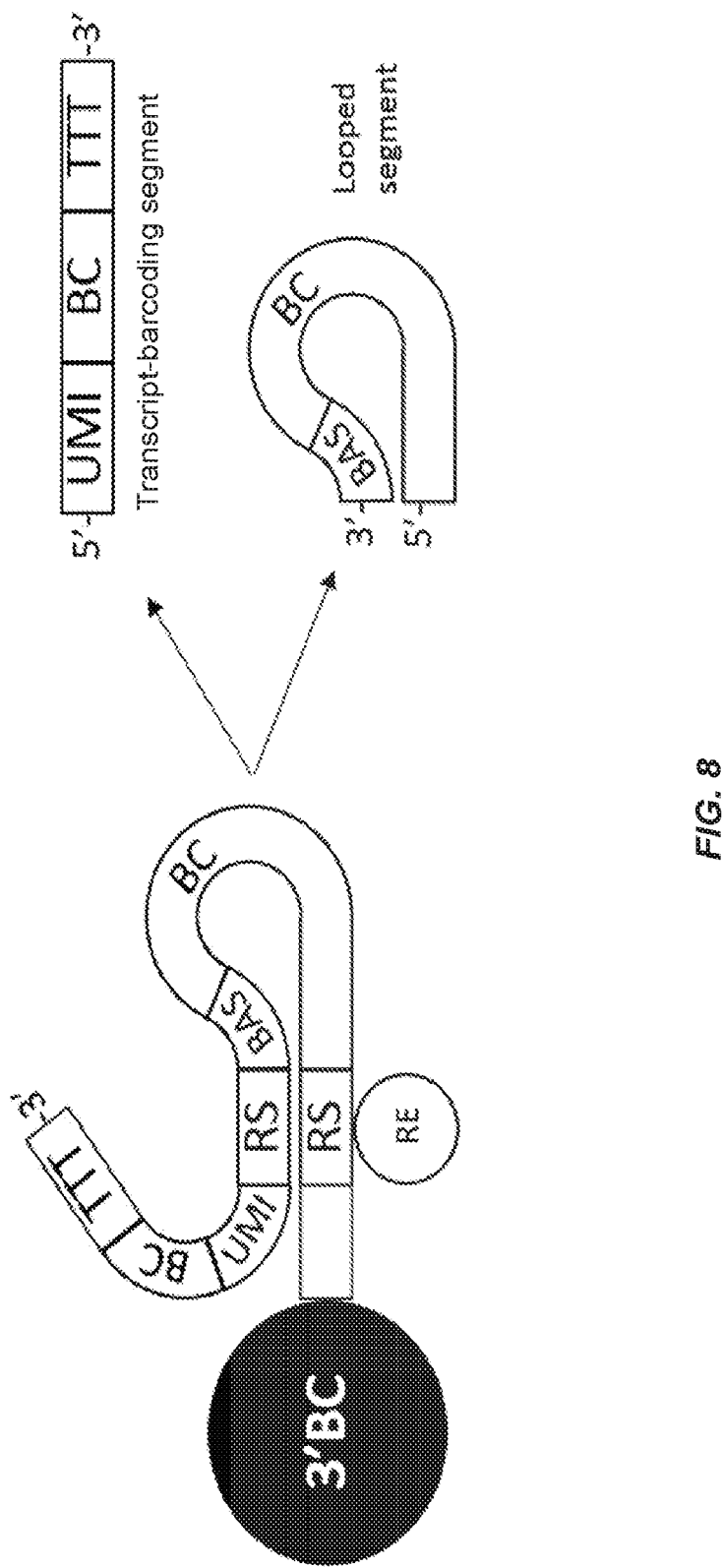

FIG. 8 is a schematic showing each bead surface-functionalized with a single-stranded barcode oligonucleotide. The oligo forms a hair-pin structure where the double-stranded segment contains a restriction site. A restriction enzyme cleaves both strands and releases the transcript-barcoding segment and the looped segment. The looped segment includes a barcode that is either identical to or simply associated with the barcode on the transcript-barcoding segment, and a "barcode association segment" (BAS). The BAS allows multiple looped segments to prime off of one another in a DNA polymerase reaction that physically links the two barcodes of the two looped segments together in a single amplicon. To accomplish this, the BAS may be palindromic, or can be comprised of discrete sets (e.g. two complementary sequences) both of which are incorporated on each bead.

Figure 9:
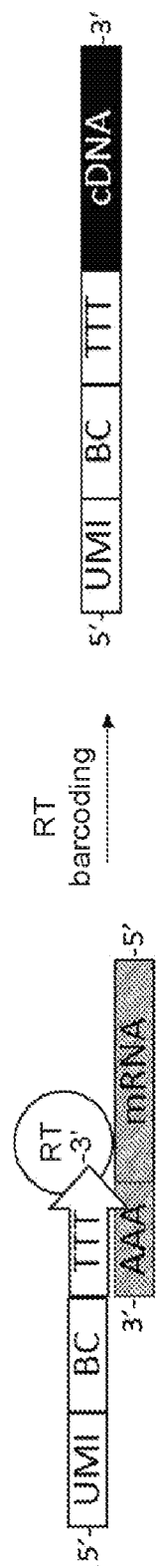

FIG. 9 is a schematic showing the transcript-barcoding segment with a poly-T tail that selectively anneals to the poly-A tail of mRNA. The transcript sequence is reverse transcribed into a single cDNA that also carries the barcode.

Figure 10:
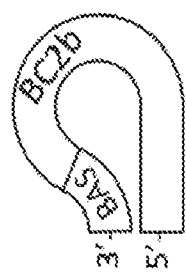
Figure 10:
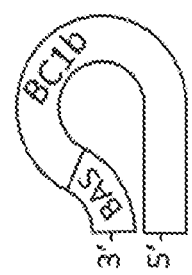

FIG. 10 is a schematic showing that when two barcoded beads are co-encapsulated with a cell, each transcript from that cell may be barcoded by either of the two barcodes (BC1a or BC2a). The same droplet will also contain many copies of the looped segment that correspond to each of those two transcript barcodes.

Figure 11:
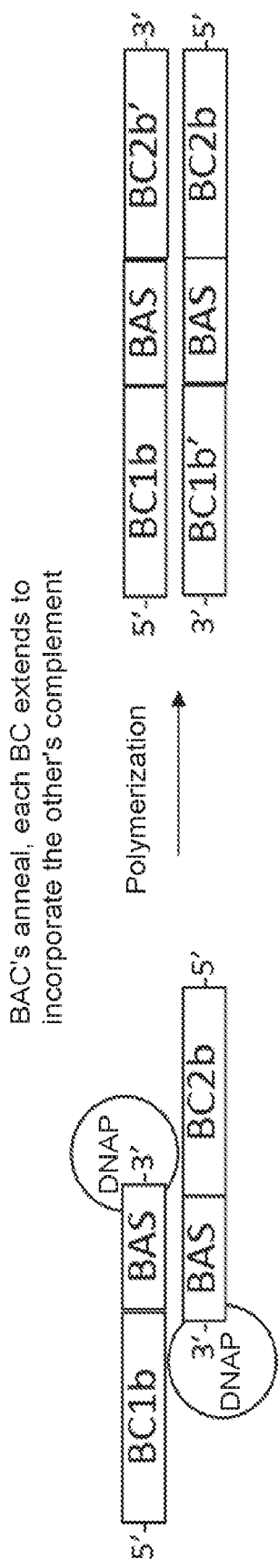

FIG. 11 is a schematic showing looped segments can be designed such that cross-annealing between looped segments via the BAS is preferred vs. a single looped segment remaining self-annealed in a looped structure. DNA polymerase can be included to extend each looped segment to incorporate the complement of the other barcode.

Figure 12:
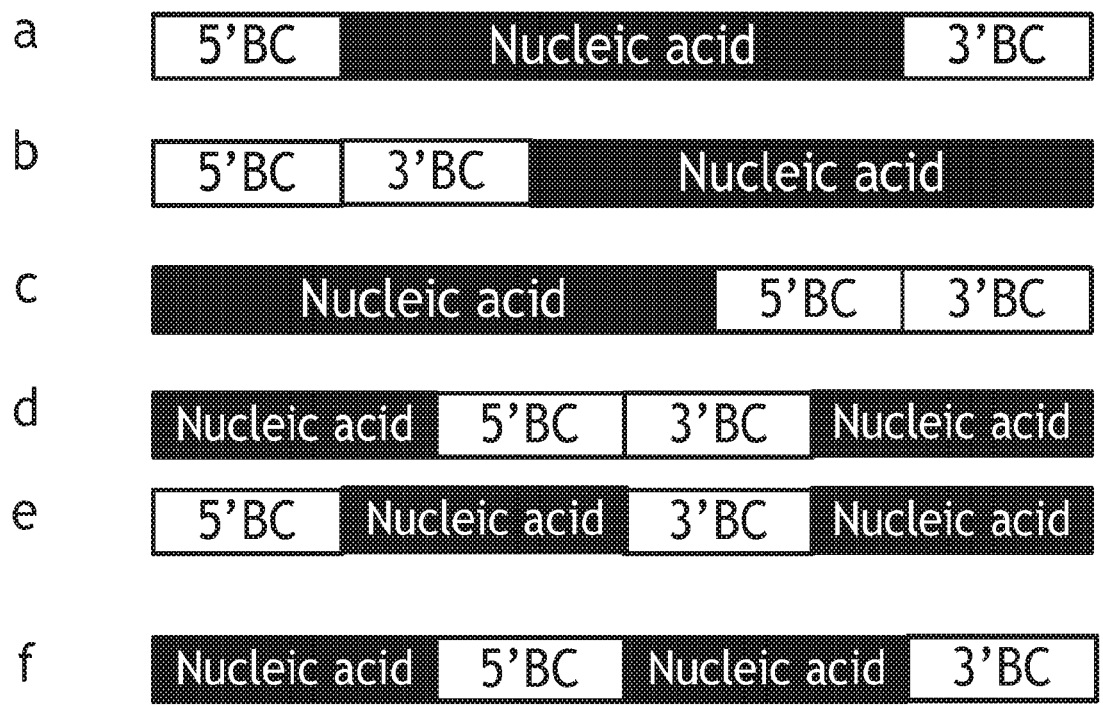

FIG. 12 is a schematic showing barcodes associated with a sample. 5' barcodes (5'BC) or 3' barcodes (3'BC) can be associated with a sample either: (a) one on each end of a nucleic acid associated with a sample, or (b) both on the 5' end of a nucleic acid or (c) both on the 3' end of a nucleic acid or (d-f) internally, either within a nucleic acid or in which case 2 nucleic acids associated with a sample are covalently linked. Barcodes can be added to a sample through known methods, including but not limited to ligation or amplification technologies such as polymerase chain reaction (PCR).

Figure 13:
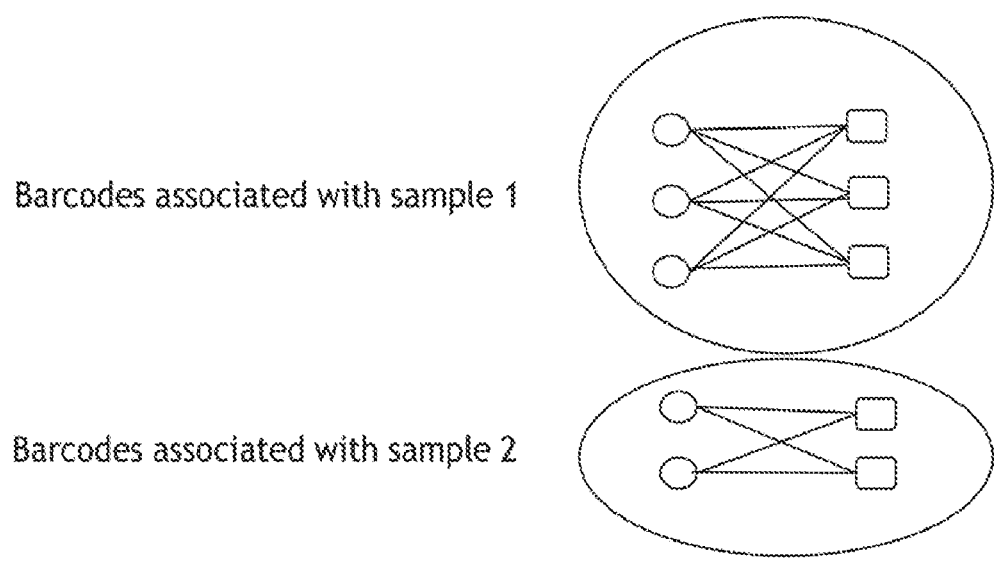

FIG. 13 is a schematic showing analysis of barcode sets associated with a sample. Barcoded nucleic acids can be represented as a bipartite graph in which round vertices (5' barcodes) and rectangle vertices (3' barcodes) are connected by an edge (representing a nucleic acid). In a reaction container, all combinations of 5' and 3' barcodes can be associated with nucleic acids, and hence all round vertices should be connected to all rectangle vertices by edges, forming a maximal clique. Using maximal cliques will correctly associate the barcodes and nucleic acids within a sample.

Figure 14:
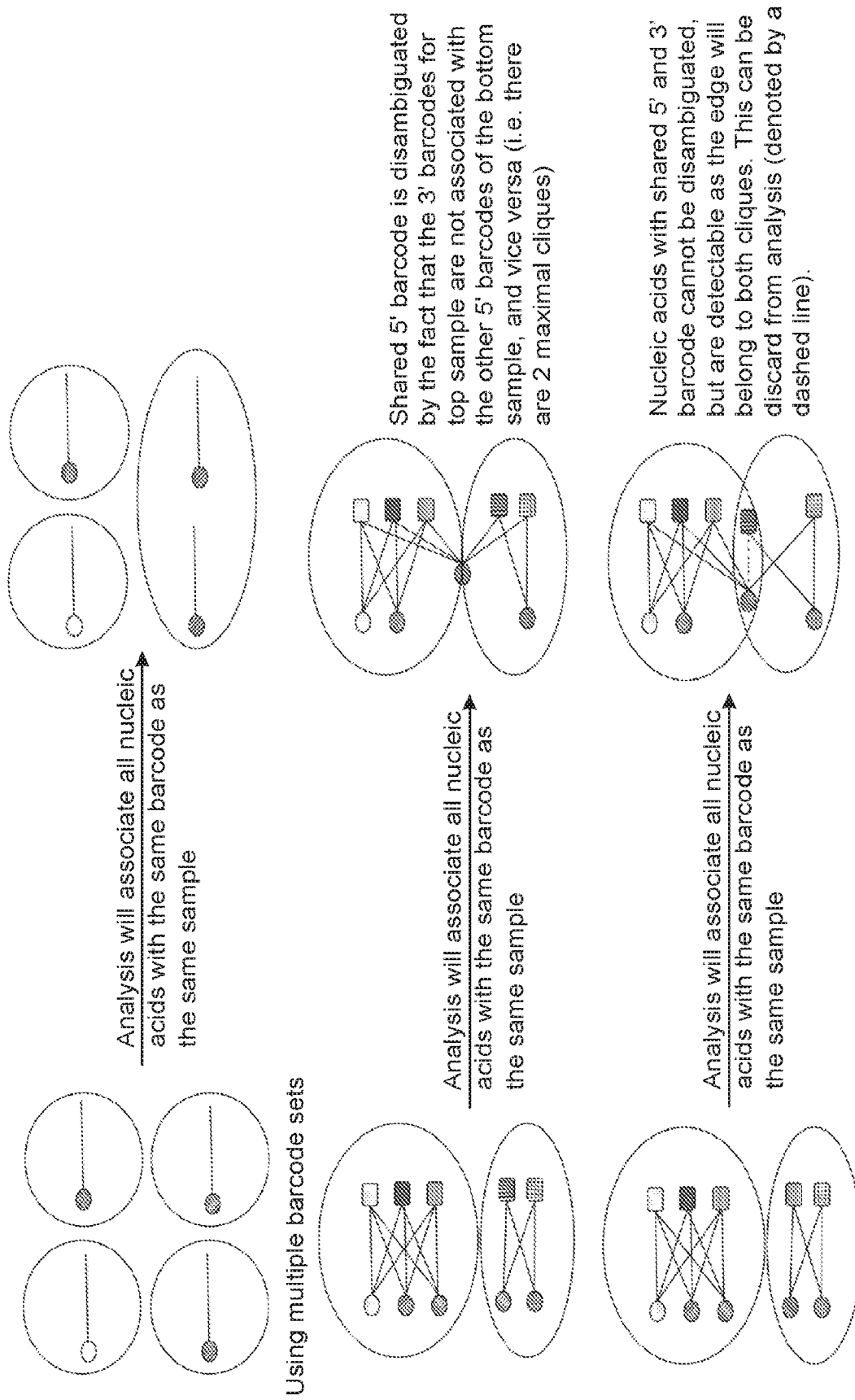

FIG. 14 is a schematic showing multiple barcode sets associated with a sample resolve barcode 'collisions'. (Top) If single barcode sets are used and different reaction containers happen to contain identical barcode beads, erroneous association of nucleic acids from different samples will occur. (Middle) If multiple barcode sets are used the identical barcode in both reaction containers (a 5' barcode) can be disambiguated by their association with the other barcode set (here, the 3' barcodes). The shared 5' barcode will belong to both cliques but edges (representing the nucleic acids) from the 5' barcode vertices will uniquely belong to only 1 clique. (Bottom) If there is an identical 5' and 3' barcode in two reaction containers, the edge will belong to both cliques and it is not known which sample the nucleic acids are associated with. This can be detected and discarded from analysis (denoted by a dashed line).

Figure 15:
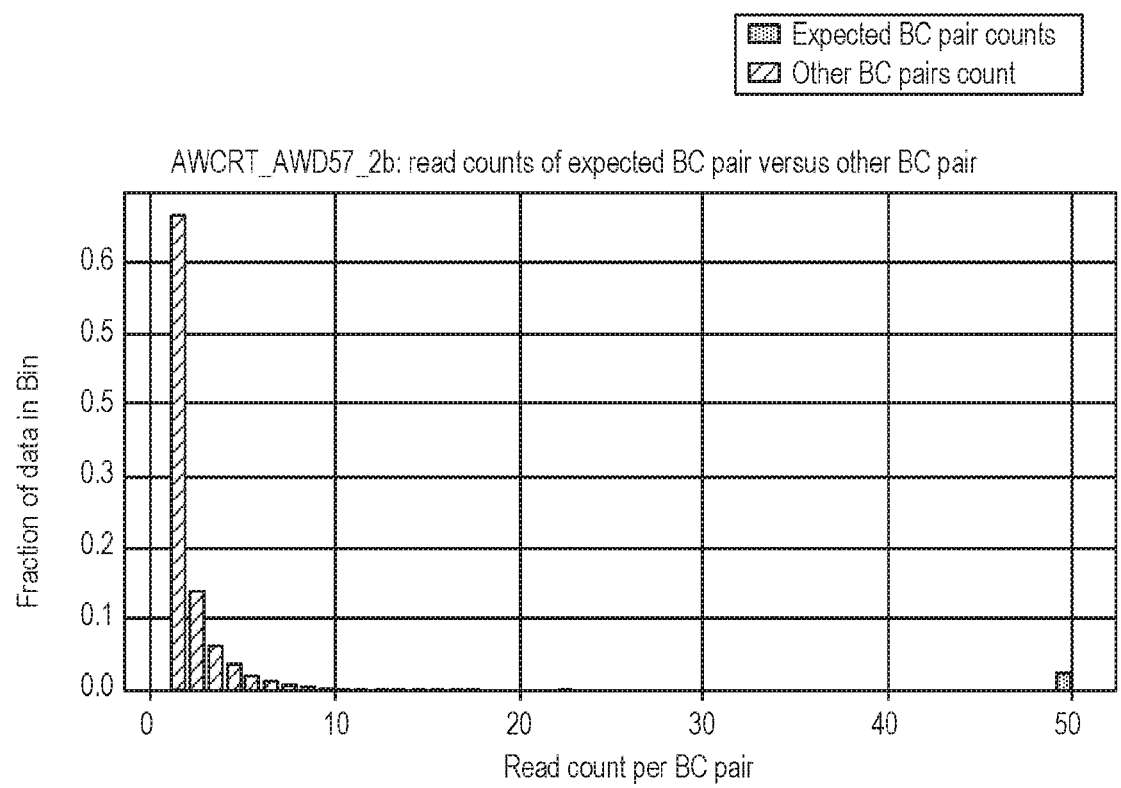

FIG. 15 is a graph showing the frequency of barcode pairs (y-axis, fraction) observed in sequence read pairs versus number of times observed (x-axis, count). More than half of barcode pairs were observed exactly once, consistent with these representing experimental noise (such as sequencing errors) that could be straightforwardly filtered out. Few barcode pairs were observed more than 10 times. The bin at 50 includes all pairs of barcodes that were observed 50 or greater times.

DETAILED DESCRIPTION OF THE INVENTION

Rather than attempting to introduce a single, unique barcode into the reaction containers, the present application is directed to the deliberate introduction, in most or all cases of a productive reaction, multiple barcodes that form a distinguishable barcode set that identifies the cell of origin for all genomic or transcriptomic targets in that container. This can be implemented in any of several different ways, and the critical common feature is that when multiple barcodes are introduced into a single container, in addition to barcoding the genomic or transcriptomic targets of interest, a mechanism also exists by which all barcodes in the container can be associated with all other barcodes in that container, either directly or indirectly. When multiple rather than single barcodes are assigned to individual containers, random distribution of barcodes can be applied without requirement that a majority of containers be empty and therefore unproductive. The provided methods also reduce the inefficiency of applying the intersection of two or more Poisson distributions.

To demonstrate the benefit of such a barcoding scheme in terms of throughput and coverage, consider the case where at least 95% of containers receiving a cell and a barcode receive exactly one cell and one barcode. In the multi-barcode scheme, the corresponding requirement is that greater than 95% of containers receiving a cell receive exactly one cell since the number of barcodes received is now for practical considerations irrelevant. This mark is reached with an average value of 0.1 cells per container, in which case 95.1% of containers that receive at least one cell will receive exactly one cell. The average number of barcodes per container can be chosen based on the desired balance between barcode economy, complexity of downstream analysis, and sample coverage among other factors. For an average value of three barcodes per container, the corresponding Poisson distribution dictates that 95.02% of containers will receive at least one barcode. Whereas in the single-barcode approach fewer than 0.24% of containers receive at least one cell and one barcode and thus have the opportunity to participate productively in the genomic or transcriptomic profiling system, in this analogous multi-barcode approach, 9.04% of containers receive at least one cell and one barcode. This is a nearly forty-fold increase in the number of potentially productive containers, and the resulting throughput (in terms of the number of cells profiled) can be expected to increase accordingly. Importantly, this reflects not only the number but also the percentage of cells that are profiled. Whereas in the single-barcode approach only 4.88% of containers receive at least one barcode and so a correspondingly low percentage of cells are profiled, in the multi-bead approach with an average value of three barcodes per container, 95.02% of containers receive at least one barcode. This allows for a nearly twenty-fold increase in sample coverage, and an even greater gain can be realized if a higher average number of barcodes per container is chosen. This improvement in sample coverage is extremely beneficial and especially so for applications where the profile of a relatively rare cell clone is sought.

Another benefit of the multi-barcode approach is that the scheme is robust to the polyclonality that is a common result of most or all methods that aim to produce sets of monoclonal barcodes. Whereas in the single-barcode approach a single set that contains two or more distinct barcodes would confound the profile of the cell to which that barcode set is assigned, a profiling scheme that associates all barcodes in a given container together into a comprehensive barcode set is able to cope with a polyclonal barcode set. It also can enable significant improvements in terms of yield and/or cost to the bead barcoding process. Using the emulsion PCR-based method described here as an example, if the tolerable threshold is such that at least 95% of barcoded beads must be monoclonal, the barcode copy lambda during the emulsification process must be set to 0.1 with the result that fewer than 10% of beads will receive a barcode and the remainder of beads are wasted. If the system is designed so that a larger proportion of polyclonal beads are tolerable—e.g. 99% of beads must be mono-, double-, or triple-coded (in this case ~70% are mono-coded)—the barcode copy lambda can be set to 0.7 with the result that >50% of beads receive at least one barcode. This leads to more than a five-fold increase in production yield.

TABLE 1

Percent clonality of beads as a function of the average copy number of barcodes per droplet (lambda) in the emPCR bead barcoding reaction along with corresponding fold-increase of barcoded bead yield vs. the case of lambda = 0.1.

| b.c. lambda | Clonality | | | | Throughput fold increase vs 0.1 lambda |
| --- | --- | --- | --- | --- | --- |
| | Single | Double | Triple | Quad | |
| 0.1 | 95.1% | 4.8% | 0.2% | 0.0% | NA |
| 0.2 | 90.3% | 9.0% | 0.6% | 0.0% | 1.9 |
| 0.3 | 85.7% | 12.9% | 1.3% | 0.1% | 2.72 |
| 0.4 | 81.3% | 16.3% | 2.2% | 0.2% | 3.46 |
| 0.5 | 77.1% | 19.3% | 3.2% | 0.4% | 4.13 |
| 0.6 | 73.0% | 21.9% | 4.4% | 0.7% | 4.74 |
| 0.7 | 69.1% | 24.2% | 5.6% | 1.0% | 5.29 |

By identifying individual genetic or transcriptomic profiles using distinguishable sets of barcodes rather than by single barcodes, the scheme can also identify instances wherein any one barcode enters into multiple reaction containers. The association of a single barcode sequence with two otherwise distinct sets will allow such cases to be identified and either classified by a separate analysis mechanism or discarded.

The correct assignment of barcodes and nucleic acids associated with a sample can be done using graph theory, specifically, using a bipartite graph and searching for maximal cliques. A bipartite graph is a graph whose vertices (or nodes) can be divided into two disjoint sets in which every edge connects a vertex in the $1^{st}$ set to a vertex in the $2^{nd}$ set. For our purpose, the two sets of vertices represent the two barcode sets (5' and 3' barcode sets) and the edge that connects the vertices represents the nucleic acid that has that 5' barcode and that particular 3' barcode incorporated into it (FIG. 13). In a reaction container, all combinations of 5' and 3' barcodes can be associated with nucleic acids, and hence all round vertices should be connected to all rectangle vertices by edges, forming a maximal clique. A clique is a subset of vertices of an undirected graph such that every two distinct vertices in the clique are adjacent. A maximal clique is a clique that cannot be extended by including one more adjacent vertex, meaning it is not a subset of a larger clique. Informatically solving for maximal cliques using a computer program will correctly associate the barcodes and nucleic acids within a sample (see FIGS. 13 and 14). FIG. 14 illustrates an additional advantage of using multiple barcode sets. Instances wherein any one barcode enters into multiple reaction containers (or barcode 'collisions') can be detected and resolved. This is not possible when using only one barcode.

The combination of multiple barcodes within a functional set inherently adds greater diversity to the code space. For example, in one possible embodiment of the invention where each cDNA copy receives one barcode at each end (5' and 3') and the code space in each set (5' and 3') is 100, the overall code space of the system is 100×100=10,000 possible barcode combinations. This can allow for a smaller library of barcoded beads to be produced in order to barcode a larger number of cells with greater barcoding fidelity.

For convenience, the barcode sets are referred to as 5' and 3' barcodes. Multiple barcode sets can be used to assign the nucleic acids to the appropriate reaction container and therefore identify the origin of the nucleic acid sample. Barcodes sets can be associated with the nucleic acid sample either at the 5' end and 3' end, or both at the 5' end, or both at the 3' end, or even internally within the nucleic acid sample (see FIG. 12). Barcodes can be added to nucleic acids using methods known in the art, such as but not limited to amplification (such as polymerase chain reaction (PCR), ligation and transposition reactions (please see Green et al., Molecular Cloning, A Laboratory Manual, 4$^{th}$ Edition, Cold Spring Harbor Press (2012)). As long as at least two or more barcode sets are associated with the nucleic acid sample, nucleic acids can be assigned to the appropriate reaction container (and thus sample) with all the advantages mentioned herein, including beating Poisson statistics in loading reaction containers with barcode beads and resolving barcode 'collisions', in which any one barcode enters into multiple reaction containers.

The inclusion of multiple barcoded beads in a single droplet is also likely to benefit the molecular biology through which the gene or transcript barcoding reaction is to proceed. Since the barcode nucleic acid molecules are a reactant in the barcoding reaction and the efficiency of any reaction is directly related to the supply of its reactants, it follows that the inclusion of multiple barcodes in each reaction will lead to increased yield of barcoded product.

Provided herein are methods of identifying the origin of a nucleic acid sample. The methods include forming a reaction mixture comprising a nucleic acid sample comprising nucleic acid molecules from a single cell and a set of barcodes, incorporating the set of barcodes into the nucleic acid molecules of the sample, and identifying the set of barcodes incorporated into the nucleic acid molecules of the single cell thereby identifying the origin of the nucleic acid sample. Optionally, the set of barcodes comprises at least two 5' nucleic acid constructs each construct comprising a unique 5' barcode. Optionally, the set of barcodes comprises at least two 3' nucleic acid constructs each construct comprising a unique 3' barcode. Optionally, one or more of the nucleic acid molecules comprises two or more unique barcodes. Optionally, the unique barcodes are located at the 5' end, the '3' end or both the 5' and 3' end of the nucleic acid molecules. Optionally, the method comprises forming a plurality of reaction mixtures. Optionally, two or more unique barcodes are present in 30%, 40%, 50%, 60%, 70%, 80%, 90% or 100% of the reaction mixtures. Optionally, forming the plurality of reaction mixtures comprises adding the set of barcodes to the plurality of reaction mixtures at a lambda greater than 0.5, 0.6, 0.7, 0.8, 0.9, 1.0, 2.0, 3.0, 4.0 or 5.0.

Also provided are methods of identifying the origin of a nucleic acid sample that include providing a set of 3' nucleic acid constructs each construct comprising a unique 3' barcode sequence, providing a nucleic acid sample comprising nucleic acid molecules from a single cell, contacting the nucleic acid sample with the set of 3' nucleic acid constructs, incorporating into the nucleic acid molecules the 3' barcode sequences from the 3' nucleic acid constructs, and identifying the set of 3' barcode sequences thereby identifying the origin of the nucleic acid sample from the single cell.

As the term is used herein, "incorporating" a sequence into a polynucleotide refers to covalently linking a series of nucleotides with the rest of the polynucleotide, for example at the 3' or 5' end of the polynucleotide, by phosphodiester bonds, wherein the nucleotides are linked in the order prescribed by the sequence. A sequence has been "incorporated" into a polynucleotide, or equivalently the polynucleotide "incorporates" the sequence, if the polynucleotide contains the sequence or a complement thereof. Incorporation of a sequence into a polynucleotide can occur enzymatically (e.g., by ligation or polymerization) or using chemical synthesis (e.g., by phosphoramidite chemistry).

The term "primer" refers to a polynucleotide (oligonucleotide) and analogs thereof that are capable of selectively annealing or hybridizing to a target nucleic acid. A primer serves as an initiation primer for DNA synthesis under suitable conditions, such as in the presence of appropriate enzyme(s), cofactors, substrates, e.g., nucleotides (dNTPs) and the like. A primer allows the synthesis of a sequence complementary to the corresponding polynucleotide template, flanking sequence or amplification product from the primer's 3' end. Typically a primer can be between about 10 to 100 nucleotides in length. A primer binding site or universal priming sequence refers to a nucleic acid sequence to which a primer is capable of binding to initiate amplification.

As used herein, the terms "amplify" and "amplification" refer to enzymatically copying the sequence of a polynucleotide, in whole or in part, so as to generate more polynucleotides that also contain the sequence or a complement thereof. The sequence being copied is referred to as the template sequence. Examples of amplification include DNA-templated RNA synthesis by RNA polymerase, RNA-templated first-strand cDNA synthesis by reverse transcriptase, and DNA-templated PCR amplification using a thermostable DNA polymerase. Amplification includes all primer-extension reactions.

As used herein, the term "isothermal" refers to a reaction, such as an enzymatic reaction, that is carried out at a constant temperature or range of temperatures.

The term "associated" is used herein to refer to the relationship between a sample and the DNA molecules, RNA molecules, or other polynucleotides originating from or derived from that sample. The term can be used to refer to the relationship between one barcode sequence and another barcode sequence or between one barcode sequence and a set of other barcode sequences. For example, a barcode is associated with another barcode if the barcodes are in the same set of barcodes. Alternatively, a barcode can be associated with a set of barcodes if the barcode sequence is one of the barcodes in the set of barcode sequences. A polynucleotide is associated with a sample if it is an endogenous polynucleotide, i.e. it occurs in the sample at the time the sample is selected, or is derived from an endogenous polynucleotide. For example, the mRNAs endogenous to a cell are associated with that cell. cDNAs resulting from reverse transcription of these mRNAs, and DNA amplicons resulting from PCR amplification of the cDNAs, contain the sequences of the mRNAs and are also associated with the cell. The polynucleotides associated with a sample need not be located or synthesized in the sample, and are considered associated with the sample even after the sample has been destroyed (for example, after a cell has been lysed). Molecular barcoding or other techniques can be used to determine which polynucleotides in a mixture are associated with a particular sample.

As the term is used herein, a "reaction volume" (or equivalently a "container" or "compartment") is a space where a volume of liquid, for example an aqueous solution, can be held and remain segregated (e.g., isolated) from other such volumes of liquid or the surrounding medium. The segregation between a reaction volume and its surroundings can result from solid barriers around the reaction volume or from phase separation. For example, an aqueous microfluidic droplet suspended in a hydrophobic carrier fluid can constitute a reaction volume because water is immiscible in the carrier fluid. Thus, two droplets that are separated from each other in the carrier fluid remain segregated, and nucleic acids or other hydrophilic species dissolved in one droplet cannot exit the droplet or transit to another droplet. Reaction volumes can also be defined by, for example, flasks, beakers, centrifuge tubes, and wells in a multi-well plate.

"Adding" a set of barcodes to the RNAs associated with a sample, e.g., from a single cell, involves forming a reaction mixture containing the barcodes and a single cell or the RNAs from a single cell, such that the RNAs and barcodes can take part in a barcoding reaction. Once added, the barcodes can react directly with one or more RNAs, for example by hybridizing with an RNA, or can take part in a polymerization reaction or series of reactions (for example, reverse transcription or RT-PCR) in which RNA molecules serve as templates.

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, can be modified. Typical modifications include methylation, biotinylation, and other art-known modifications. In addition, a polynucleotide can be single-stranded or double-stranded and, where desired, linked to a detectable moiety. In some aspects, a polynucleotide can include hybrid molecules, e.g., comprising DNA and RNA.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in nucleotide sequences by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods described herein.

As used herein, and unless otherwise indicated, the term "complementary," when used to describe a first nucleotide sequence in relation to a second nucleotide sequence, refers to the ability of a polynucleotide comprising the first nucleotide sequence to hybridize and form a duplex structure under certain conditions with a polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Complementary sequences include base-pairing of a region of a polynucleotide comprising a first nucleotide sequence to a region of a polynucleotide comprising a second nucleotide sequence over the length or a portion of the length of one or both nucleotide sequences. Such sequences can be referred to as "complementary" with respect to each other herein. However, where a first sequence is referred to as "substantially complementary" with respect to a second sequence herein, the two sequences can be complementary, or they may include one or more, but generally not more than about 5, 4, 3, or 2 mismatched base pairs within regions that are base-paired. For two sequences with mismatched base pairs, the sequences will be considered "substantially complementary" as long as the two nucleotide sequences bind to each other via base-pairing.

"Complementary" sequences, as used herein, may also include, or be formed entirely from, non-Watson-Crick base pairs and/or base pairs formed from non-natural and modified nucleotides, in as far as the above embodiments with respect to their ability to hybridize are fulfilled. Such non-Watson-Crick base pairs includes, but are not limited to, G:U Wobble or Hoogstein base pairing.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information web-site. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands.

Identical sequences include 100% identity of a polynucleotide comprising a first nucleotide sequence to a polynucleotide comprising a second nucleotide sequence over the entire length of one or both nucleotide sequences. Such sequences can be referred to as "fully identical" with respect to each other herein. However, in some aspects, where a first sequence is referred to as "substantially identical" with respect to a second sequence herein, the two sequences can be fully complementary, or they may have one or more, but generally not more than about 5, 4, 3, or 2 mismatched nucleotides upon alignment. In some aspects, where a first sequence is referred to as "substantially identical" with respect to a second sequence herein, the two sequences can be fully complementary, or they may be at least about 50, 60, 70, 80, 81, 82, 83, 84, 85, 86, 87, 88, 89, 90, 91, 92, 93, 94, 95, 96, 97, 98, or 99% identical to each other. To determine the percent identity of two nucleotide sequences described herein, the default settings of BLASTN described above can be used.

Where a first sequence is referred to as "distinct" with respect to the identity of a second sequence herein, the two sequences have at least one or more mismatched nucleotides upon alignment. In some aspects, distinct sequences can have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more mismatched nucleotides upon alignment. In some aspects, distinct sequences can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 81, 82, 83, 84, 85, 86, 87, 88, 89, 90, 91, 92, 93, 94, 95, 96, 97, 98, 99, or less than 100% identical to each other. In some aspects, where a first sequence is referred to as "distinct" with respect to a second sequence herein, the two sequences can have substantially or fully identical sequences, but instead differ from one another based upon differing patterns of modification within the sequences. Such modifications are generally known in the art, e.g., methylation.

In some aspects, a polynucleotide can be present in a library of polynucleotides. In some aspects, a polynucleotide library can include a plurality of polynucleotides. In some aspects, each polynucleotide in the plurality of polynucleotides can be derived from a single sample. In some aspects, a single sample is a single cell.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand."

The term "messenger RNA" or "mRNA" refers to an RNA that is without introns and that can be translated into a polypeptide.

The term "cDNA" refers to a DNA that is complementary or identical to an mRNA, in either single stranded or double stranded form.

The term "amplicon" refers to the amplified product of a nucleic acid amplification reaction, e.g., RT-PCR.

The term "hybridize" refers to a sequence specific non-covalent binding interaction with a complementary nucleic acid. Hybridization may occur to all or a portion of a nucleic acid sequence. Those skilled in the art will recognize that the stability of a nucleic acid duplex, or hybrids, can be determined by the Tm. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

As used herein, "region" refers to a contiguous portion of the nucleotide sequence of a polynucleotide. Examples of regions are described herein an include identification regions, sample identification regions, barcode regions, binding regions, cDNA regions, and the like. In some aspects, a polynucleotide can include one or more regions. In some aspects, a polynucleotide can include less than 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more regions. In some aspects, regions can be coupled. In some aspects, regions can be operatively coupled. In some aspects, regions can be physically coupled.

As used herein, "barcode" or "barcode sequence" refers to any unique sequence label that can be coupled to at least one nucleotide sequence for, e.g., later identification of the at least one nucleotide sequence.

As used herein, a "barcode set" or a "set of barcodes" refers to any unique set of sequences that can be coupled to nucleotide sequences from a sample, where a nucleotide sequence is coupled to one barcode sequence in the set, for, e.g., later identification of the nucleotide sequences.

The terms "barcode construct", "barcoded construct", and "barcode construct molecule" are used interchangeably herein to refer to an oligonucleotide that comprises a unique barcode sequence.

Figure 2A:
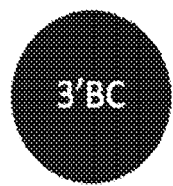
FIG. 2 is a schematic showing an exemplary composition of two bead sets (3' and 5'). The barcode nucleic acids on each 3' bead comprise a restriction site (RS) that is used to cleave the barcode sequence from the bead, a unique molecular identifier sequence (UMI) that is used in downstream analysis, a barcode sequence (BC3), and a poly-T sequence (TTT). The barcode nucleic acids on each 5' bead comprise a restriction site (RS), a barcode sequence (BC5), and three guanine residues.
Figure 2B:
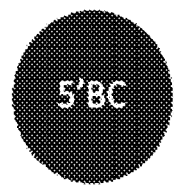

The terms "3' nucleic acid construct" or "3' nucleic acid barcode construct" refers to an oligonucleotide that comprises a barcode sequence that is 3' to the "5' nucleic acid barcode construct." The 3' nucleic acid construct can be incorporated into a nucleic acid molecule, e.g., the 3' end of an mRNA. The term "3' barcode" or "3' barcode sequence" refers to a barcode located on a 3' nucleic acid construct or 3' nucleic acid barcode construct. Typically, the 3' nucleic acid constructs contain a sequence complementary to a sequence at the 3' end of a nucleic acid molecule, e.g., the 3' nucleic acid construct includes a poly-T sequence complementary to the poly-A sequence of an mRNA. Typically, the 3' construct binds to the 3' end of an mRNA sequence and is reverse transcribed to generate a cDNA molecule comprising the 3' nucleic acid construct at its 5' end. See, e.g., FIGS. 2 and 3. It can also be incorporated into a nucleic acid at the 5' end, 3' end or internally (where it is incorporated into the 3' end of a nucleic acid and a 5' end of another nucleic acid, forming one longer nucleic acid). See, e.g., FIG. 12. A 3' nucleic acid barcode construct can include, in addition to a barcode sequence, a universal priming sequence or universal priming region, and a binding site.

The terms "5' nucleic acid construct" or "5' nucleic acid barcode construct" refer to an oligonucleotide that comprises a barcode sequence that is 5' to the "3' nucleic acid barcode construct." The 5' nucleic acid construct can be incorporated into a nucleic acid molecule, e.g., the 5' end of an mRNA or 3' end of a cDNA. The term "5' barcode" or "5' barcode sequence" refers to a barcode located on a 5' nucleic acid construct or 5' nucleic acid barcode construct. Typically, the 5' nucleic acid construct contains a sequence complementary to a sequence at the 3' end of a nucleic acid molecule, e.g., the 5' nucleic acid construct includes a poly-G sequence complementary to a poly-C sequence incorporated into the 3' end of a cDNA sequence. The 5' nucleic acid construct can be incorporated into the 3' end of a cDNA molecule comprising the 3' nucleic acid construct. See, e.g., FIGS. 2 and 3. It can also be incorporated into a nucleic acid at the 5' end, 3' end or internally (where it is incorporated into the 3' end of a nucleic acid and a 5' end of another nucleic acid, forming one longer nucleic acid). See, e.g., FIG. 12. A 5' nucleic acid barcode construct can include, in addition to a barcode sequence, a universal priming sequence or universal priming region, and a binding site.

As used herein, "barcode construct bead" refers to a bead coupled to one or more barcode constructs.

As used herein, "barcoding mix" refers to a composition comprising one or more barcode constructs. The mix can include additional reagents for lysing cells, reverse transcription, restriction enzyme digestion and/or carrying out a barcoding reaction.

As used herein, "barcoding" or "barcoding reaction" refers to a reaction that links a barcode sequence, or the complement of a barcode sequence, with a nucleic acid. The barcode construct need not necessarily be covalently linked with the nucleic acid, but the barcode sequence information itself is linked with or incorporated into the nucleic acid. "Barcoding nucleic acids", "barcoding cells", "barcoding nucleic acids from cells", "barcoding nucleic acids from reaction containers", and "barcoding reaction containers" are used interchangeably.

As used herein "identification region" refers to a nucleotide sequence label (e.g., a unique barcode sequence) that can be coupled to at least one nucleotide sequence for, e.g., later identification of the at least one nucleotide sequence. In some aspects, a barcode set is used as a sample identification region.

As used herein "adapter region" or "adapter molecule" refers to a linker that couples a first nucleotide sequence to a second nucleotide sequence. In some aspects, an adapter region can include a contiguous portion of nucleotide sequence that acts as a linker.

The term "sample" can include RNA, DNA, a single cell or multiple cells or fragments of cells or an aliquot of body fluid, taken from a subject (e.g., a mammalian subject, an animal subject, a human subject, or a non-human animal subject). Samples can be selected by one of skill in the art using any means now known or later discovered including centrifugation, venipuncture, blood draw, excretion, swabbing, ejaculation, massage, biopsy, needle aspirate, lavage sample, scraping, surgical incision, laser capture microdissection, gradient separation, or intervention or other means known in the art. Samples can also be selected by one of skill in the art using one or more markers known to be associated with a sample of interest. Samples can also be selected using methods known in the art such as cell sorting and FACS.

The methods of the present invention can be practiced with any desired samples. In some embodiments, each sample includes a cell, and can be for example a single cell. A cell can be enclosed in a reaction volume such as a microfluidic droplet, and if desired can be lysed to release RNA molecules into the reaction volume. For this purpose, the cell can be contacted with a lysis buffer at any convenient time.

Provided herein are methods of identifying the origin of a nucleic acid sample. Optionally, the methods include forming a reaction mixture comprising a nucleic acid sample comprising nucleic acid molecules from a single cell and a set of barcodes, incorporating the set of barcodes into the nucleic acid molecules of the sample, and identifying the set of barcodes incorporated into the nucleic acid molecules of the single cell thereby identifying the origin of the nucleic acid sample. Optionally, forming the reaction mixture comprises contacting the single cell with the set of barcodes and lysing the cell to provide the nucleic acid sample from the single cell. Optionally, forming the reaction mixture comprises providing cells in a suspension buffer and contacting the suspension buffer comprising the cells with a barcoding buffer comprising the set of barcodes under conditions to form the reaction mixture comprising the single cell and the set of barcodes. Optionally, the reaction mixture is a droplet.

As provided herein, a set of barcodes comprises one or more copies of at least two unique barcodes. Thus, for example, a set of barcodes can include one or more of 5' nucleic acid constructs each comprising a unique 5' barcode and one or more of 3' nucleic acid constructs each comprising a unique 3' barcode. Optionally, the set of barcodes comprises at least two 3' nucleic acid constructs each construct comprising a unique 3' barcode. Optionally, the set of barcodes comprises 1, 2, 3, 4, 5, 6, 7, or 8 5' nucleic acid constructs and 1, 2, 3, 4, 5, 6, 7, or 8 3' nucleic acid constructs. Each of the 1, 2, 3, 4, 5, 6, 7, or 8 types of nucleic acid construct has a unique barcode sequence and can be provided in multiple copies. Optionally, the set of barcodes comprises two different 5' nucleic acid constructs comprising two different 5' barcodes and two different 3' nucleic acid constructs comprising two different 3' barcodes. Optionally, the set of barcodes comprises three different 5' nucleic acid constructs comprising three different 5' barcodes and three different 3' nucleic acid constructs comprising three different 3' barcodes. Optionally, the set of barcodes comprises two different 3' nucleic acid constructs comprising two different 3' barcodes and three different 5' nucleic acid constructs comprising three different 5' barcodes. Multiple copies of each type of nucleic acid construct can be provided each of the multiple copies of the same type having the same barcode. Thus, for example, a set of barcodes can include multiple copies of 1, 2, 3, 4, 5, 6, 7, or 8 different types of 5' nucleic acid or 3' nucleic acid constructs each of the different types having a unique 5' or 3' barcode sequence. Stated another way, a set of barcodes can comprise one or more copies of one or more of a first, second, third, fourth, fifth, sixth, seventh or eighth type of 5' nucleic acid construct and one or more copies of one or more of a first, second, third, fourth, fifth, sixth, seventh or eighth type of 3' nucleic acid construct. Optionally, a set of barcodes comprises one or more copies of one or more of a first, second, third, fourth, fifth, sixth, seventh or eighth type of 3' nucleic acid construct. Constructs can be RNA or DNA molecules, or RNA-DNA hybrids. For example, a construct can include RNA nucleotides covalently linked to DNA nucleotides in a common oligonucleotide strand. A construct can also be single-stranded or double stranded. If double-stranded, the construct can have one or more blunt ends or ends with single-stranded overhangs.

Also provided herein is a method of identifying the origin of a nucleic acid sample using a set of 3' nucleic acid constructs. The method includes providing a set of 3' nucleic acid constructs each construct comprising a unique 3' barcode sequence, a binding sequence, and a barcode association sequence, providing a nucleic acid sample comprising nucleic acid molecules from a single cell, contacting the nucleic acid sample with the set of 3' nucleic acid constructs, separating the 3' barcode sequence and binding sequence from the barcode association sequence, incorporating into the nucleic acid molecules the 3' barcode sequences from the 3' nucleic acid constructs, and identifying the set of 3' barcode sequences using the barcode association sequences thereby identifying the origin of the nucleic acid sample from the single cell. Optionally, the set of 3' nucleic acid constructs comprises 2, 3, 4, 5, 6, 7, or 8 3' nucleic acid constructs. Optionally, multiple copies of the 3' nucleic acid construct are attached to a solid surface, e.g., a bead, microbead, microparticle, microsphere, nanobead or hydrogel. Optionally, each bead comprises the same nucleic acid construct and multiple beads can be provided in a set of barcodes. Thus, optionally, each solid surface, e.g., bead, contains multiple copies of the same type of 3' nucleic acid construct. Thus, for example, a set of barcodes can include a first surface comprising multiple copies of a first 3' nucleic acid construct comprising a unique 3' barcode and a second surface comprising multiple copies of a second 3' nucleic acid construct comprising a unique 3' barcode different from the barcode on the first construct.

Optionally, forming the reaction mixture comprises providing cells in a suspension buffer, and contacting the suspension buffer with a barcoding buffer comprising the 5' and/or 3' nucleic acid constructs under conditions to form the reaction mixture comprising the single cell. The reaction mixture includes at least two constructs each construct having a unique barcode and a single cell. Optionally, the reaction mixture comprises at least one 5' nucleic acid construct and at least one 3' nucleic acid construct. Optionally, the reaction mixture comprises at least two 3' nucleic acid constructs. Optionally, forming the reaction mixture comprises providing a cells in a suspension buffer, and contacting the suspension buffer with a first barcoding buffer comprising the 5' nucleic acid constructs and a second barcoding buffer comprising the 3' nucleic acid constructs under conditions to form the reaction mixture comprising the single cell and at least one 5' nucleic acid construct and at least one 3' nucleic acid construct. Optionally, the reaction mixture comprises the nucleic acid sample from the single cell, at least one bead comprising multiple copies of the 5' nucleic acid constructs, and at least one bead comprising multiple copies of the 3' nucleic acid construct.

Cells can be advantageously suspended in a cell suspension buffer comprising an osmoprotectant prior to lysis. The osmoprotectant can protect the cells from osmotic stress and ensure that cellular physiology remains stable or unperturbed prior to barcoding. In some embodiments, cells are suspended in the cell suspension buffer along with barcode constructs. In some embodiments, cells are suspended in the cell suspension buffer before being contacted with reagents for reverse transcription, PCR, and/or lysis. The cell suspension buffer can be included in any reaction volume and is compatible with the methods described herein for forming and combining aqueous reaction volumes.

Cells are suspended in the cell suspension buffer before being contacted with reagents for reverse transcription, PCR, and/or lysis. The cell suspension buffer can be included in any reaction volume and is compatible with the methods described herein for forming and combining aqueous reaction volumes.

Optionally, each 5' nucleic acid construct is provided in multiple copies attached to a solid surface. Optionally, each 3' nucleic acid construct is provided in multiple copies attached to a solid surface. Examples of solid supports having solid surfaces that can be used in the present methods and compositions include beads, chromatographic resins, multi-well plates, microcentrifuge tubes, or any other objects having solid surfaces. Optionally, the solid surface is a bead, microbead, microparticle, microsphere, nanoparticle, nanobead, or hydrogel. Thus, a barcode construct can be bound to a solid support using any desired mechanism or capture chemistry, for example a biotin-avidin, biotin-streptavidin, or gold-thiol interaction. Optionally, any solid surface to which a barcode construct is attached is contacted with an aqueous solution, and barcode constructs are released into this solution. The aqueous solution can be in the same reaction volume as the RNA molecules associated with the sample, e.g., from a single cell, to which the barcode construct is to be added. Alternatively, the aqueous solution contacting the solid surface for a barcode construct can be held in a different reaction volume from the target RNAs or cells, and barcode constructs can be added to these RNAs or cells upon combining the two reaction volumes to generate a reaction mixture comprising a set of barcodes and a single cell or RNA sample from a single cell.

Provided are methods for attaching a polynucleotide to a solid support, wherein the polynucleotide contains a barcode sequence. The polynucleotide can be a barcode construct. Optionally, the methods involve generating a hydrophilic compartment (i.e., an aqueous droplet) of an inverse emulsion. The compartment can be generated as desired, for example by mixing an aqueous solution in a hydrophobic carrier fluid and optionally agitating the mixture. The aqueous solution can have a solid support, oligonucleotides, and reagents suspended therein, so that each compartment contains all necessary components for attaching the polynucleotide to the solid support when the compartment is formed. In these embodiments, prior to adding the solid support to the compartment, an oligonucleotide is bound to the surface of the solid support via a capture moiety. This oligonucleotide is referred to herein as the "bound oligonucleotide" and contains a 3' sequence complementary to a 3' sequence of a barcode oligonucleotide. The polynucleotide is thus formed on the solid support through a polymerase extension reaction involving the bound oligonucleotide and barcode oligonucleotide, and this reaction takes place within the compartment.

Optionally, when the hydrophilic compartment is formed, the barcode oligonucleotide is present at a low or limiting concentration (for example, one molecule per compartment). This concentration is convenient when a library of barcode oligonucleotides having randomized sequences is used to prepare a plurality of barcode construct beads. If every barcode oligonucleotide is assumed to have a different barcode sequence, and the solid support in each compartment is desired to have only one barcode sequence, then one barcode oligonucleotide (at most or on average) can be present per compartment. Once this condition is met, multiple solid supports (e.g., multiple beads) can be present in a compartment, or multiple copies of the bound oligonucleotide can be bound to each solid support, but all polynucleotides resulting from the polymerase extension reaction in the compartment will contain the same barcode sequence.

Solid supports for use in the present methods include beads, for example spherical beads made of metals and/or polymeric materials and having diameters in the range of ~0.1 to 10 micrometers. Beads having other characteristics can be used instead or in addition. The solid support can be functionalized with a capture moiety to attach the bound oligonucleotide to the surface. Examples of capture moieties include avidin, streptavidin, biotin, carboxyl groups, epoxy groups, hydroxyl groups, thiol groups, and gold. Some capture moieties have binding partners to which they bind specifically and non-covalently. For example, streptavidin takes biotin as its binding partner. Such a capture moiety can be coupled directly (e.g., covalently) to the solid support, and the binding partner can be coupled to the bound oligonucleotide, or vice versa, so that the bound oligonucleotide is bound to the solid support through a non-covalent interaction. Other capture moieties provide a direct covalent linkage between the bound oligonucleotide and solid support.

The bound oligonucleotide is preferably a single-stranded DNA molecule that is bound to the solid support at its 5' end. Thus, 3' end of the bound oligonucleotide is free in solution and, when hybridized to the barcode oligonucleotide, can be extended by an enzyme such as DNA polymerase. The extension reaction is templated using the barcode oligonucleotide, so that the barcode sequence gets incorporated into the DNA strand bound to the bead. If desired, the bound oligonucleotide and/or the barcode oligonucleotide can have sequences designed to minimize intramolecular secondary structure.

Any of the methods described herein for attaching polynucleotides to solid supports can be used to prepare one or more solid supports for use in barcoding samples, cells, or RNAs. The polynucleotide(s) attached to each solid support includes barcode sequences and can serve as a barcode construct. The present methods can also be used to prepare a barcode library, which includes a plurality of solid supports, each associated with a barcode sequence. Any two solid supports (for example, beads) can have barcode sequences that differ from each other in whole or in part. Optionally, every solid support in the barcode library is associated with a different barcode sequence.

A barcode construct bead prepared according to the present methods includes a bead bound to a barcode construct. The bead can be bound to multiple copies of the barcode construct, for example at least 10, 30, 100, 300, 1,000, 3,000, 10,000, 30,000, 100,000, 300,000, or 1,000,000 copies. Optionally, each copy of the barcodes constructs bound to one bead includes the same barcode sequence. The present methods also allow preparation of a beaded barcode library comprising a plurality of barcode construct beads. Every bead in the library can be associated with a different barcode sequence, and copies of barcode constructs on each bead can comprise the same barcode sequence.

Optionally, the present methods can be used to prepare a polynucleotide library by physically capturing cDNAs prepared from or obtained from one or more samples (e.g., cells) on barcode construct beads. Each bead includes a barcode construct with a cDNA binding site at the 3' end. The bead can be contacted with an enzyme to render the binding site single-stranded (for example, leaving a 3' overhang at the end of the template molecule free in solution). The bead is then contacted with one or more cDNAs from a sample such that the cDNAs bind to copies of the template molecule through the binding sites. In preferred embodiments, the binding site includes one or more G nucleotides, for example a poly-G tract, and is complementary to the non-templated poly-C tract added to the end of cDNAs by reverse transcriptase.

The beads in a polynucleotide library can be used as desired, for example to sequence the cDNAs from a plurality of samples or separate the cDNAs from different samples. In the latter case, beads corresponding to different samples can be pelleted using centrifugation or magnetism, and then resuspended and separated using standard methods. If desired, following the binding of cDNAs to template molecules on a bead, the template molecules can be enzymatically extended, thereby incorporating the cDNA sequences into DNA duplexes bound the bead and associating these sequences with a barcode sequence. If the number of copies of cDNA molecules from a sample is comparable to the number of copies of the barcode construct on a bead, then these cDNA molecules can be captured on a small number of beads (for example, at most about 1, 3, 10, 30, 100, 300, or 1000 beads per sample). RNAs from samples can be reverse transcribed using standard methods or as discussed above to generate cDNA.

A variety of methods can be used to release 5' and 3' nucleic acid constructs when they are bound to solid surfaces to allow incorporation of the constructs comprising the barcodes into the nucleic acids of a nucleic acid sample. For example, each 5' and 3' nucleic acid construct can include a photocleavable linker or a restriction enzyme site. Optionally, each 5' nucleic acid construct further comprises a photocleavable linker and each 3' nucleic acid construct further comprises a restriction enzyme site. Optionally, each 5' nucleic acid construct further comprises a restriction enzyme site and each 3' nucleic acid construct further comprises a photocleavable linker. Optionally, the method further comprises contacting the reaction mixture with a restriction enzyme and exposing the reaction mixture to UV light to release the 5' and 3' nucleic acid constructs from the solid surface. Optionally, the 5' and 3' nucleic acid constructs further comprise a restriction enzyme site and the method further comprises contacting the reaction mixture with a restriction enzyme to release the 5' and 3' nucleic acid constructs from the solid surface. Optionally, the 5' and 3' nucleic acid constructs further comprise a photocleavable linker and the method further comprises exposing the reaction mixture to UV light to release the 5' and 3' nucleic acid constructs from the solid surface.

As noted above, optionally, the 3' nucleic acid construct comprises a unique 3' barcode sequence, a binding sequence and a barcode association sequence. Optionally, the 3' nucleic acid construct is capable of forming a hairpin. Optionally, the 3' barcode sequence and binding sequence are separated from the barcode association segment by a restriction enzyme sequence or photocleavable linker. Optionally, a restriction enzyme releases the 3' barcode sequence from the solid surface and separates the binding sequence from the barcode association segment. Optionally, UV light releases the 3' barcode sequence from the solid surface and separates the binding sequence from the barcode association segment. Optionally, the binding sequence on the 3' nucleic acid constructs comprises a poly-T sequence. Optionally, the binding sequence of the 3' nucleic acid constructs binds to the poly-A sequences on the nucleic acid molecules of the sample. Optionally, the barcode sequences on the 3' nucleic acid constructs are incorporated by reverse transcription. Optionally, the reverse transcription produces nucleic acid molecules comprising the 3' barcode sequence. Optionally, the barcode association segment comprises a priming sequence. Optionally, the priming sequence is a palindromic sequence. Optionally, the priming sequence of one barcode association segment is capable of binding the priming sequence of any other barcode association segment in the nucleic acid sample. Optionally, the barcode association segments that have contacted each other are extended by a DNA polymerase to incorporate both barcode association segments into a single nucleic acid.

Restriction enzymes and restriction enzyme sites are known and the enzymes are commercially available. Restriction enzyme digestion refers to catalytic cleavage of a nucleic acid molecule with an enzyme that functions only at specific locations in a nucleic acid molecule. The uses of such enzymes is understood by those of skill in the art. Thus, the 5' and 3' nucleic acid constructs can contain endonuclease restriction sites that facilitate cleavage of the construct upon exposure to an appropriate enzyme (e.g., a restriction endonuclease). Optionally, the restriction enzyme is selected from the group consisting of Nb.BsrDI, Nb.Btsl, Nt.BbvCI, Nt.BspQI, Nt.BsmAI, Nt.BstNBI, Nt.AlwI, and Nt.BsmAI. Optionally, the 5' or 3' nucleic acid construct attached to a solid surface is double stranded and only one strand of the construct is released from the solid surface. Thus, optionally, the 5' and/or 3' nucleic acid constructs can include a nicking endonuclease restriction site, and the strands can be released using one or more nicking endonuclease enzymes. The nicking endonuclease restriction site can be a site specific for an enzyme selected from the group consisting of Nb.BsrDI, Nb.Btsl, Nt.BbvCI, Nt.BspQI, Nt.BsmAI, Nt.BstNBI, Nt.AlwI, and Nt.BsmAI. Optionally, a strand-displacing DNA polymerase can be included with the restriction enzyme. The strand-displacing polymerase can be added before, simultaneously or after the nicking endonuclease enzyme. The strand-displacing DNA polymerase can be selected from the group consisting of Klenow exo-, Bst Large Fragment and engineered variants of Bst Large Fragment Photocleavable linkers and their methods of use are also known. As used herein, the term "photocleavable linker" refers to any chemical group that attaches or operably links two molecules, e.g., two nucleic acids or a nucleic acid and a solid surface. Optionally, the linkers comprise a 2-nitrobenzyl moiety. See, e.g., U.S. Pat. No. 5,643,722, which is incorporated by reference herein in its entirety. Photocleavable linkers also include, but are not limited to, alpha-substituted 2-nitrobenzyl moieties [e.g. 1-(2-nitrophenyl) ethyl moieties], 3,5-dimethoxybenzyl moieties, thiohydroxamic acid, 7-nitroindoline moieties, 9-phenylxanthyl moieties, benzoin moieties, hydroxyphenacyl moieties, and NHS-ASA moieties. The linker can be cleaved by exposure to light of appropriate wavelength, such as for example, ultra violet light, to harvest the nucleic acid molecules from the substrate (see J. Olejnik and K. Rothschild, Methods Enzymol 291:135-154, 1998).

Optionally, the provided constructs can include a unique molecular identifier (UMI) sequence. Optionally, a UMI sequence contains randomized nucleotides and is incorporated into the barcode construct independently of the barcode sequence. Thus, a set of barcode constructs containing the same barcode sequence can contain different UMI sequences. Where the set of barcode constructs containing the same barcode sequence but different UMI sequences is added to the RNAs associated with one sample, every RNA sequence can be linked to a different UMI sequence during barcoding. Barcode construct beads with UMI sequences can be generated where the constructs on each bead contain the same barcode sequence and a library of different UMI sequences.

Figure 3:
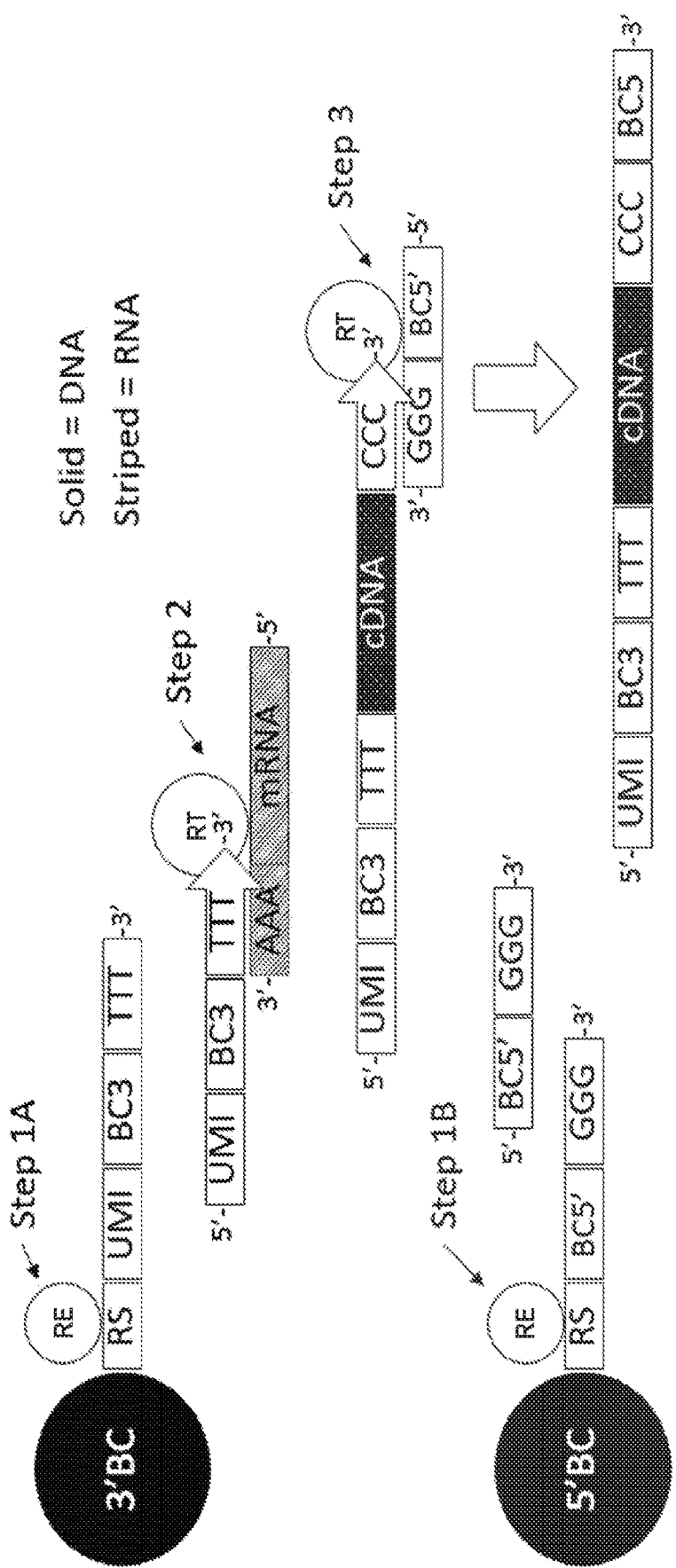
FIG. 3 is a schematic showing that within the droplet the cell is lysed and mRNA transcripts are released and accessible to the barcoding reaction. A restriction enzyme (RE) cleaves both the 3' and 5' barcodes from their beads at the restriction site. Reverse transcription is initiated when the poly-T sequence of the 3' barcode anneals to the poly-A tail at the 3' end of an mRNA transcript. Starting from this 3' barcode primer, the reverse transcriptase (RT) enzyme reverse transcribes in the 5' to 3' direction to produce a single cDNA amplicon that includes both the 3' barcode and the mRNA sequence. Upon reaching the end of the transcript, the RT enzyme (an M-MLV enzyme) adds several cytosine residues that provide an annealing site for the three guanine residues of the 5' barcode. Once the 5' barcode has annealed, the RT enzyme "template-switches" and incorporates the 5' barcode sequence into the same cDNA.

A barcode construct can include, in addition to a barcode sequence, a universal priming sequence or universal priming region, and a binding site. Thus, optionally, the 3' nucleic acid constructs and 5' nucleic acid constructs typically include a binding sequence. Optionally, the 5' and 3' nucleic acid constructs comprising a primer binding site or universal priming sequence. Optionally, the 3' nucleic acid construct has a binding sequence comprising a poly-T sequence. The poly-T sequence binds to the poly-A sequences on the nucleic acid molecules of the sample. Upon binding of a 3' nucleic acid construct to a nucleic acid molecule, the barcodes on the 3' nucleic acid constructs can then be incorporated by reverse transcription. The reverse transcription produces nucleic acid molecules comprising the 3' barcode sequence. Thus, the 3' nucleic acid construct can serve as a primer for reverse transcription. Here, the binding site of the construct is an RNA binding site (e.g., an mRNA binding site) and contains a sequence region complementary to a sequence region in one or more RNAs. Optionally, the binding site is complementary to a sequence region common to all RNAs in the sample to which the barcode construct is added. For example, the binding site can be a poly-T tract, which is complementary to the poly-A tails of eukaryotic mRNAs (FIG. 3). Alternatively or in addition, the binding site can include a random sequence tract. Upon adding the 3' constructs to the RNAs associated with a sample, reverse transcription can occur and first strands of cDNA can be synthesized, such that the 3' barcode sequence is incorporated into the first strands of cDNA. It will be recognized that reverse transcription requires appropriate conditions, for example the presence of an appropriate buffer and reverse transcriptase enzyme, and temperatures appropriate for annealing of the barcode construct to RNAs and the activity of the enzyme. It will also be recognized that reverse transcription, involving a DNA primer and an RNA template, is most efficient when the 3' end of the primer is complementary to the template and can anneal directly to the template. Accordingly, the 3' nucleic acid construct can be designed so that the binding site occurs at the 3' end of the RNA.

As discussed above, optionally, a set of 3' nucleic acid constructs is used comprising a barcode, a binding sequence and a barcode association sequence. Optionally, the 3' nucleic acid constructs comprising a primer binding site or universal priming sequence. Each construct can be a single-stranded DNA oligo that forms a hairpin structure. Optionally, the constructs are linear. If the constructs for a hairpin, in the double-stranded segment of the hairpin, a restriction site can be incorporated that directs the restriction of both strands. This cleaves and separates the barcode and binding region from the separate, looped segment that may also contain a barcode, as well as the "barcode association sequence" (BAS). See, e.g., FIG. 8. A linear oligo can be used with multiple restriction sites that also results in two or more segments being cut from the bead. The barcode region includes a barcode, a poly-T segment and optionally a UMI. This segment anneals to the poly-A tail of mRNA transcripts released by the cell within the droplet and primes reverse transcription of that mRNA sequence, thus incorporating the barcode into the cDNA produced. See, e.g., FIG. 9. Separately, the looped segment comprises a barcode of its own that is either identical to or corresponds to the barcode from which it was cleaved. When multiple beads are co-encapsulated with a cell, the two transcript barcoding segments (BC1a & BC2a, FIG. 10) will both serve as primers for the RT barcoding reaction, and the transcriptome from that cell will incorporate both barcodes. Separately, the two corresponding looped segments carrying their respective barcodes (BC1b & BC2b, FIG. 10) will also be present. Binding regions on the BAS will enable the BC1b and BC2b looped segments to cross-anneal, and a DNA polymerase can be included in the reaction mix to extend each segment to incorporate the complement of the other barcode (FIG. 11). In this way, the BAS' are physically linked in single amplicons which can then be sequenced downstream in order to associate the barcodes as a set to unify the transcriptome from that cell. The binding sequence on the BAS can be a palindromic sequence or each BAS can include a sequence complementary to a sequence on another BAS as described further in the examples.

When using 5' and 3' nucleic acid constructs, once the 3' nucleic acid construct has been incorporated into a first strand of cDNA, optionally, the reverse transcriptase enzyme adds two to five cysteine resides to the end of the nucleic acid molecules in the sample. The two to five cysteine residues provides a binding sequence complementary to a binding sequence on the 5' nucleic acid constructs. Optionally, the binding sequence on the 5' nucleic acid constructs comprises a poly-G sequence. The binding sequence on the 5' nucleic acid constructs can then bind to poly-C sequences on the nucleic acid molecules of the sample. The 5' nucleic acid construct is incorporated into the nucleic acid sample using a reverse transcriptase enzyme. See., e.g., FIG. 3. This process has been described at least in WO 2012/148497, which is incorporated by reference herein in its entirety. Briefly, H-MMLV reverse transcriptases have a 3' dC tailing activity and add non-templated dCs to 1st strand cDNA. If a barcoded construct ending in at least 1 G is also present, e.g., a 5' nucleic acid construct, the construct can base-pair with the 3' dC of the 1st strand cDNA and the reverse transcriptase undergoes template switching and continues transcription. The reverse transcriptase thus covalently adds the barcode sequence to the 3' end of the 1st strand cDNA via phosphodiester bonds. The resulting construct, e.g., as shown in FIG. 7, is a nucleic acid molecule generically comprising the sequence from 5' to 3': 5' barcode-cDNA sequence-3' barcode. Optionally, the nucleic acid sample is further amplified to produce multiple copies of the plurality of nucleic acid sequences each sequence comprising a 5' barcode and a 3' barcode. Optionally, the 5' and 3' nucleic acid constructs comprise universal priming sites used for amplifying the nucleic acid sequences comprising the '5 and 3' barcodes.

Optionally, the reverse transcriptase is an M-MLV enzyme. Optionally, the reverse transcriptase is MMLV H-reverse transcriptase.

As noted above, reverse transcription can occur if lysis reagents are present in the droplet to release RNAs from the cell, and if reverse transcriptase, primers, and other appropriate reagents are present. Enzymes and reagents for facilitating lysis and reverse transcription can be added all at once, for example by merging a droplet containing the enzymes and reagents with the droplet containing the barcodes and cell, or can be added in steps.

Optionally, the 5' nucleic acid construct is a double stranded nucleic acid construct comprising a promoter and wherein the 5' nucleic acid construct serves as a template to produce multiple copies of the 5' nucleic acid construct. Optionally, the promoter is an RNA polymerase promoter. See, e.g., FIG. 7. Thus, optionally, the 5' nucleic acid is a double-stranded DNA (dsDNA) template molecule having the following sequence: 5'-T7 promoter-universal priming sequence-barcode sequence-binding sequence-3'. The T7 promoter sequence allows for synthesis of an the 5' nucleic acid construct from the template by T7 RNA polymerase. The universal priming sequence is used for complementarity to PCR primers that are used downstream. The binding sequence consists of 1 or more guanine bases (G's) and allows for complementary base-pairing of the barcoded construct to the 3' end of 1st strand cDNA. Other promoter sequences can be used, such as but not limited to T3 and SP6 promoter sequences, which allows for synthesis of an RNA barcoded construct by T3 and SP6 RNA polymerases respectively. Other RNA polymerases which do not have a specific promoter sequence may also be used, as long as a full length or near full length 5' nucleic acid construct is synthesized in a large fraction of cases.

The provided nucleic acid sample is from a single cell and the RNAs associated with the sample can include mRNAs. The sample can include, for example, at least 1, 3, 10, 30, 100, 300, 1,000, 3,000, 10,000, 30,000, 100,000, 300,000, or 1,000,000 mRNA molecules, which can represent any number of genes, alleles, reading frames, or distinct sequences. Optionally, the RNAs associated with the sample include all mRNAs from the sample, a full or partial transcriptome of the cell, or the total RNA from the cell.

Without being bound by any theory, the present methods place no limits on the number of RNAs that can be barcoded per sample, Accordingly, the number of polynucleotides of interest produced per sample can be at least 10, 30, 100, 300, 1,000, 3,000, 10,000, 30,000, 100,000, 300,000, or 1,000, 000. Each polynucleotide of interest can be present in multiple copies. Furthermore, the number of cells or samples that can be barcoded in one execution of the method is limited only by the challenges (discussed above) of preparing many sets of barcodes with a unique combination of barcode sequences. In some embodiments, the one or more samples include at least 10, 30, 100, 300, 1,000, 3,000, 10,000, 30,000, 100,000, 300,000, or 1,000,000 cells. Samples (for example, each being a single cell) can be obtained from the same subject or different subjects. For example, at least 2, 3, 4, 5, 6, 7, 8, 9, 10, 20, 30, 40, 50, 60, 70, 80, 90 or 100 different subjects can provide samples.

The combination of 5' and 3' barcodes in the nucleic acid sample identifies the origin of the nucleic acid sample from a single cell. Optionally, the barcodes in the nucleic acid sample are identified by sequencing. Each barcode sequence is expected to be associated with assembled contigs from different samples as barcode sequences are reused in unique barcode sets. The term contig as used herein refers to overlapping sequence data (reads). Identical contigs may be observed to be using barcode sequences a, b and c. And barcode sequences a, b and d may be observed to be associated with another contig. From this, it can be then concluded that a, b and c comprise barcode set 1, and a, b and d barcode set 2. Barcode set 1 is associated with the nucleic acid sample from one cell while barcode set 2 is associated with the nucleic acid sample from a second different cell. As all 5' barcodes in a set are associated with all 3' barcodes in a set, they can be represented in graph theory as maximal bipartite cliques (See FIG. 13). Maximal bipartite cliques will associate barcode sets and nucleic acids with the single cell.

Also provided are compositions generated using the methods disclosed herein. Accordingly, the present application provides compositions of RNA and DNA constructs for their generation. Also provided are barcode construct bead libraries, emulsion droplet libraries loaded with RNA barcode constructs, emulsions containing barcode construct libraries with cells, barcoded cDNA libraries, and microfluidic droplet generating devices, among others.

Provided are compositions comprising a population of barcoded beads. The compositions include a plurality of beads each bead having attached to its surface multiple copies of a 5' or 3' nucleic acid construct. Thus, provided are composition is provided having a plurality of beads each bead having attached to its surface multiple copies of a 5' nucleic acid construct. Also provided are compositions comprising a plurality of beads each bead having attached to its surface multiple copies of a 3' nucleic acid construct. Optionally, the composition is a barcoding mix that when added appropriately to a suspension buffer comprising cells results in a reaction mixture comprising at least one bead comprising 5' nucleic acid constructs, at least one bead comprising 3' nucleic acid constructs and a single cell. Preferably the reaction mixture includes at least three different nucleic acid constructs, e.g., two 5' nucleic acid constructs and one 3' nucleic acid construct or two 3' nucleic acid constructs and one 5' nucleic acid construct.

Further disclosed herein are kits comprising the provided constructs described herein. A kit can comprise a plurality of solid supports coupled to barcode constructs described herein. Optionally, the kit comprises one or more barcode construct libraries each library comprising a plurality of barcode constructs with the same barcode. For example, provided is a kit comprising a library of barcode beads comprising 5' and 3' nucleic acid constructs including 1, 2, 3, 4, 5, 6, 7, 8 or more types of 5' and/or 3' nucleic acid constructs. Optionally, the kit comprises a barcoding mix and/or cell suspension buffer described herein. The kit can include instructions for use. The kits may include, in a suitable container a bead, construct, or library as disclosed herein, one or more controls, and various buffers, reagents, enzymes and other standard ingredients well known in the art. Thus, the kit can further comprise enzymes or any other reagent for carrying out cell lysis, restriction enzyme digestion and barcoding reactions.

The container can include at least one well on a plate comprising one or more wells. The container can include at least one vial, test tube, flask, bottle, syringe, droplet or other container means, into which the provided reagents, nucleic acid constructs, beads, libraries or cells may be placed, and in some instances, suitably aliquoted. Where an additional component is provided, the kit can contain additional containers into which this component may be placed. The kits can also include a means for containing the reagents, nucleic acid constructs, beads, libraries or cells and any other reagent containers in close confinement for commercial sale. Such containers may include injection or blow-molded plastic containers into which the desired vials are retained. Containers can include labeling with instructions for use and/or warnings.

Also provided are devices for generating and transporting reaction volumes such as those described in U.S. Ser. No. 14/586,857, which is incorporated by reference herein in its entirety. These volumes can occur on a microfluidic scale and can be phase-separated from a carrier fluid. Examples of reaction volumes that can be handled by the devices include aqueous droplets in an inverse emulsion (i.e., a water/oil emulsion). The devices allow barcode constructs, samples (e.g., cells), and/or RNAs obtained from these samples to be encapsulated in droplets, separately or together. The devices also allow reagents to be introduced into droplets, so that barcode constructs molecules can be enzymatically generated and the RNAs from individual samples can be barcoded.

Figure 1:
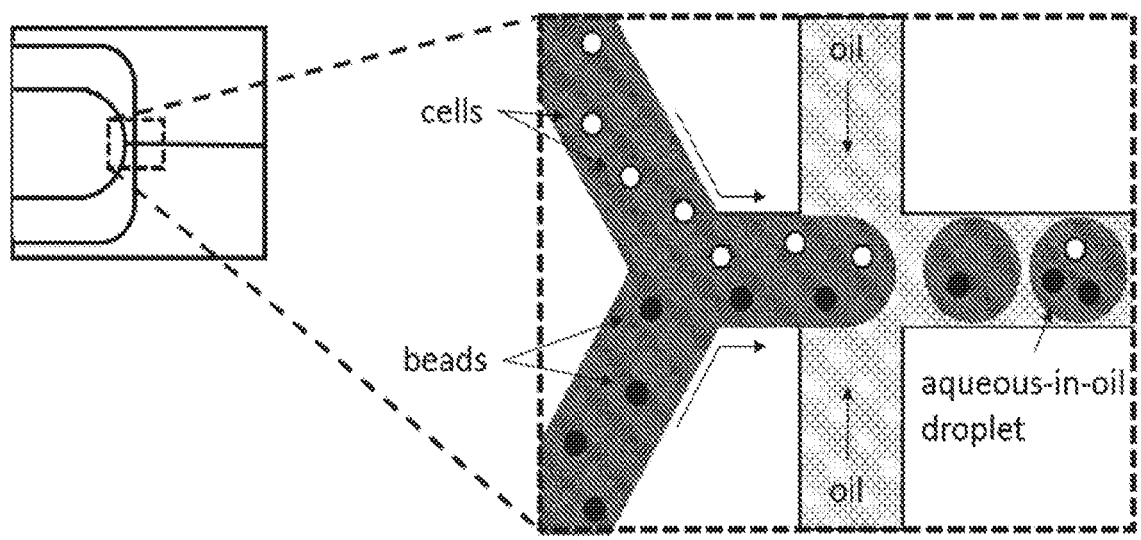
FIG. 1 is a schematic drawing of a microfluidic droplet chip with oil input channels in a flow-focusing configuration for droplet formation and the following aqueous input channels: (1) cells in a suspension buffer and (2) barcoded beads in barcoding mix. The suspension buffer and barcoding mix are located different microfluidic channels that converge to merge their components at ratios to comprise the ultimate mix that is desired in the droplets. Barcoded beads and cells are loaded into aqueous droplets as described by a Poisson distribution. The average values (lambdas) of beads per droplet and cells per droplet are a function of the concentration of those components in their input streams. The droplet is the reaction container in which the barcoding reaction takes place.

A device generally includes three microfluidic pathways, each coupled to a pressure source and a flow sensor. The pressure source for a microfluidic pathway drives fluid through the pathway, and the flow sensor, which occurs downstream of the pressure source, can be used to measure the rate of flow through the pathway. In some embodiments, the first pathway and second pathway merge at a first junction to form a combined pathway. See, e.g., FIG. 1.

Devices as described herein can be assembled from tubing and fluidics components available from IDEX Corporation (Lake Forest, Ill., U.S.A.), and using a microfluidic droplet chip available from Dolomite Microfluidics (Charlestown, Mass., U.S.A.). Some features of the microfluidic droplet chip are described in U.S. Pat. Nos. 7,268,167, 7,375,140, 7,717,615, 7,772,287, 8,741,192, and 8,883,864, which are incorporated herein by reference. Suitable pressure sources include syringe pumps and pressure pumps. Pressure pumps are available from Dolomite Microfluidics. The pressure sources can be controlled independently.

Optionally, the first and second microfluidic pathways transport aqueous solutions. Each pathway can include an injection port and a valve (e.g., a four-way valve) to bring a solution introduced in the injection port in-line with the pathway. Optionally, a reservoir holding an aqueous carrier fluid is disposed upstream of each four-way valve. The aqueous carrier fluid can mix with an aqueous solution in the four-way valve as the carrier fluid is driven downstream, or push a plug of the aqueous solution downstream toward the first junction. Optionally, a flow resistor is disposed in each microfluidic pathway.

Once an aqueous solution is introduced into the first or second microfluidic pathway, it can pass through a sample loop that meters the flow of the solution toward the first junction. Metering can be achieved as desired, for example using fluidic resistance or valves disposed along the sample loop. Optionally, one sample loop is associated with each of the first and second microfluidic pathways, and the sample loops are in contact with a thermal cooling unit. The thermal cooling unit can be included to prevent thermal denaturation of enzymes, nucleic acids, or other biological components in the aqueous solutions, or to establish optimal temperatures for enzymatic reactions. Portions of the thermal cooling unit in contact with the sample loops for the first and second microfluidic pathways can be controlled independently or jointly. Any substance or apparatus can be used as a thermal cooling unit provided that it can cause the temperatures of aqueous solutions passing through the sample loops to deviate from the ambient temperature. Examples of suitable thermal cooling devices are Peltier devices and ice bins.

Optionally, the aqueous solution transported through the first microfluidic pathway contains cells and barcode construct beads. In some embodiments, the aqueous solution transported through the second microfluidic pathway contains reagents for cell lysis and reagents for producing polynucleotides of interest (e.g., enzymes for generating barcode construct molecules). The injection port, valve, and/or sample loop associated with each microfluidic pathway can be configured or customized to accommodate the contents of the aqueous solution passing through that pathway. For example, the sample loop associated with the first microfluidic pathway can have an enlarged interior diameter to accommodate cells and beads. It will be recognized many other options exist for allocating cells, beads, and reagents between the first and second microfluidic pathways, so that all of these components are combined at the first junction. For example, cells can be transported through the first microfluidic pathway and beads can be transported through the second microfluidic pathway. Each pathway can be configured as desired, in view of the contents of the aqueous solution it carries.

The fluid pathway containing droplets, which results from the merger of the combined pathway constitutes a sample pathway. The sample pathway is delivered to a sample collection container, which occurs downstream of the second junction. In the sample collection container, droplets can be subjected to thermal cycling. The droplets can also be broken open and barcoded nucleic acids can be harvested.

In operation, the device can be used to encapsulate barcode construct beads and cells into aqueous microfluidic droplets, so that each droplet contains approximately two beads and one cell on average. The number of beads and cells in each droplet can be tuned as desired, for example by adjusting the concentrations of beads or cells in solutions loaded into the device, or by adjusting the flow rates in the three microfluidic pathways. The reagents included in each droplet allow barcode construct molecules to be enzymatically generated from the one bead in the droplet. These reagents also allow the one cell to be lysed and RNAs from the cell to undergo barcoding reactions. Thus, the RNAs from the cell can be barcoded within the droplet, and nucleic acids derived from these RNAs (and containing a barcode sequence) can be later traced to one cell when the nucleic acids from multiple cells are mixed.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims below.

EXAMPLES

Example 1. Sets of Nucleic Acid Barcodes for Analysis of Nucleic Acids Associated with a Single Cell The transcriptome of each cell is barcoded using two distinct sets of barcoded bead libraries (a 5' set and a 3' set). See FIG. 2. Each 3' barcode consists of a restriction site, a unique molecular identifier, the barcode sequence, and a poly-T sequence that will specifically target the poly-A tail of mRNA transcripts (thus avoiding ribosomal and tRNA that comprise the considerable majority of total RNA in each eukaryotic cell). Each 5' barcode comprises a restriction site (RE) that may be the same as the restriction site on the 3' bead set, the complement of the ultimate barcode sequence, and three guanine residues. These two bead sets are encapsulated in droplets along with a cell of interest. A droplet device such as the one shown in FIG. 1 can be used.

The concentration of each bead set (3' and 5') is adjusted so that the desired proportion of droplets receive at least one bead of each set. For example, for an average value of three beads of each type per droplet, more than 90% of droplets will receive at least one bead of each type. Cell concentration is similarly tuned for the optimal balance between throughput and single-cell encapsulation. For the purposes of this example, the average value is 0.1 cells per droplet, in which case greater than 95% of droplets that receive a cell will receive exactly one cell. A productive droplet will receive a cell and at least one bead from each of the 5' and 3' sets. After a successful encapsulation event, the reaction can proceed as illustrated in FIG. 3.

The mRNA is fully reverse transcribed and the incorporation of a barcode sequence on each end of the cDNA is produced. In the case where exactly one bead of each type is co-encapsulated with a cell, mRNA transcripts that are fully reverse-transcribed will exhibit the same pair of 5' and 3' barcodes, comprising the barcode set that is unique to that cell. In the case where multiple of either or both bead sets are co-encapsulated with a cell, every 5'/3' combination is expected to be represented in the cDNA library that is produced, and this set of 5'/3' combinations is the barcode set that is unique to that cell. Every cDNA will carry the 3' barcode at a minimum. In cases where reverse transcription is incomplete, the 5' barcode may not be incorporated into the cDNA. Even in such cases where only the 3' barcode is incorporated, as long as that barcode has associated with a sufficient number of 5' barcodes in that droplet to establish it as part of that barcode set, the incomplete cDNA can potentially still be assigned to its proper transcriptome in downstream analysis.

FIG. 4 illustrates the case in which multiple barcoded beads of each barcode set are co-encapsulated in a single droplet along with a cell. Due to the large number of mRNA transcripts within each cell, all 3' barcodes will have the opportunity to match with all 5' barcodes in the droplet by the barcoding scheme described above. These barcodes form a unique barcode set that identifies all transcripts originating from the cell.

In many cases, the barcoding reaction may fail to run to completion and only part of the transcript sequence will be transcribed. Though incomplete, this is potentially useful information regardless. FIG. 5 illustrates that even in cases of non-full-length cDNA that fail to incorporate a 5' barcode, these cDNAs can still be assigned to the proper barcode set. Thus, nucleic acids with only one barcode can be assigned to the correct transcriptome with a high degree of confidence (the same holds true vice-versa). The requirement for this is that the 3' barcode code space (the total number of unique 3' barcodes) is sufficiently large that any one 3' barcode is sufficiently unlikely to be co-encapsulated with multiple cells. Even in cases where that does arise, this overlap can be detected and the non-full-length cDNAs with that particular shared 3' barcode can be safely discarded. By contrast, in the case of a single barcode system, the profiles of two cells receiving the same barcodes would be merged during analysis.

FIG. 6 demonstrates that even when there is some overlap of the same individual barcodes, the set of barcodes can be distinguished by the inclusion of one unique barcode.

The required code space (the number of unique barcodes) for each of the 5' and the 3' set must be determined. Barcodes must also be sufficiently unique that they can be distinguished in the presence of sequencing errors, i.e., in the event of a small number of mis-called bases one barcode should not be converted into another. The establishment of a set of barcodes will help to resolve cases where sequencing error might create ambiguity between barcodes.

One alternative embodiment is similar to the barcoding scheme described above in that it involves template-switching, but in this case the 5' barcode bead set has a different composition, as shown in FIG. 7. This demonstrates that there are multiple approaches to a "template-switching" barcoding scheme that incorporates a barcode into each end of cDNA that is fully reverse transcribed from an mRNA transcript.

Example 2. Sets of Nucleic Acid Barcodes for Analysis of Nucleic Acids Associated with a Single Cell-Non-Template Switching This example describes a non-template-switching method. There is only a single set of barcoded beads. Each bead has a single-stranded DNA oligo that forms a hairpin structure. In the double-stranded segment of the hairpin, a restriction site is incorporated that directs the restriction of both strands. This cleaves both the transcript barcoding segment and a separate, looped segment that also contains a barcode, as well as a "barcode association sequence" (BAS). See FIG. 8.

The transcript barcode segment includes a UMI, a barcode, and a poly-T segment. This segment anneals to the poly-A tail of mRNA transcripts released by the cell within the droplet and primes reverse transcription of that mRNA sequence, thus incorporating the barcode into the cDNA produced (FIG. 9). Separately, the looped segment comprises a barcode of its own that is either identical to or corresponds to the barcode from which it was cleaved. It also comprises a priming sequence. the BAS, that is a palindromic sequence.

In the event that multiple beads are co-encapsulated with a cell, the two transcript barcoding segments (BC1a & BC2a, FIG. 10) will both serve as primers for the RT barcoding reaction, and the transcriptome from that cell will incorporate both barcodes. Separately, the two corresponding looped segments carrying their respective barcodes (BC1b & BC2b, FIG. 10) will also be present.

The palindromic BAS will enable the BC1b and BC2b looped segments to cross-anneal, and a DNA polymerase is included in the reaction mix to extend each segment to incorporate the complement of the other barcode (FIG. 11). In this way, the BAS's are physically linked in single amplicons which can then be sequenced downstream in order to associate the barcodes as a set to unify the transcriptome from that cell.

If a palindromic sequence is undesirable, a system could also be designed where the BAS comprises two complementary sequences and each bead carries both BAS sequences in roughly equal proportion. What has been described as the "looped" segment may be linear rather than looped. This depends on the restriction enzyme that is used. Similarly, rather than using a hairpin, a linear oligo can be used with multiple restriction sites that also results in two or more segments being cut from the bead. Here again, the "looped" segment may not be looped, but linear instead.

Example 3. Using Multiple Barcoding to Identify which Nucleic Acids are Associated with the Same Sample without a Priori Knowledge of What Containers the Barcodes are Located PBMCs preparation to barcode cells. Cryopreserved PBMCs were thawed and the cell pellet washed three times in phosphate buffered saline (Corning, Manassas, Va.) and either singly FACS-sorted into 96-well plates or resuspended into isotonic cell suspension buffer (CSB) comprising 25 mM NaCl and 153 mM betaine. Cells were then counted and diluted with CSB to an average of 1 cell per well for reverse transcription.

Oligo Plate preparation. Barcoded oligoDT oligos (the 3' barcode, hereafter referred to as "oDT BC") and barcoded template-switch oligos (the 5' barcode, hereafter referred to as "wID BC") were ordered from Integrated DNA Technologies (Coralville, Iowa). Upon arrival, both oDT BC and wID BC were diluted to 10 µM and keep at −20° C. until use. They have the following sequences:

TABLE 2

Oligo Sequences

| Name | Sequence |
|---|---|
| oDT BC | GGC TCG GAG ATG TGT ATA AGA GAC AG [7-mer barcode] NNN NNN NNT TTT TTT TTT TTT TTT V (SEQ ID NO: 1) |
| wID BC | GGA AGA TAG GGA TAA CAG GGT AAT G [7-mer barcode] ACG GG (SEQ ID NO: 2) |
| pltwll_LibPCR_Fw | AAT GAT ACG GCG ACC ACC GAG ATC TAC ACT CGT CGG CAG CGG AAG ATA GGG ATA ACA GGG TAA TG (SEQ ID NO: 3) |
| pltwll_LibPCR_RV | CAA GCA GAA GAC GGC ATA CGA GAT [Index sequence] GTC TCG TGG GCT CGG AGA TGT GTA TAA GAG A (SEQ ID NO: 4) |
| pltwell_PCR2_Fw | AATGATACGGCGACCAC (SEQ ID NO: 5) |
| pltwell_PCR2_Rv | CAAGCAGAAGACGGCATAC (SEQ ID NO: 6) |

The barcodes were designed such that they are at least 2 edit distance apart from one another, i.e., it takes at least 2 mutations (substitutions, insertions or deletions) to convert one barcode to another. This greatly reduces barcode assignment errors as there need to be at least 2 sequencing errors for a barcode to have a chance of being misassigned as another barcode due to these errors.

Reverse Transcription and barcoding. 96-well plates were prepared containing oDT BC and wID BC distributed into each well via random Poisson distribution with a lambda of 2. With such a distribution, some wells would receive no oligos, and others would receive multiple oligos, and on average each well would receive 2 oligos. A random Poisson distribution script was written in R to determine which oligos would be placed into each well, and a liquid handler (FeliX, Cybio, Germany) was used to distribute the barcodes into the wells. Reactions were performed in RT buffer comprising 6 mM Mg2+, 0.3% Tween20, RNase inhibitor, Maxima H Minus Reverse Transcriptase and bovine serum albumin (BSA) in each well. In each well, the samples were single cells deposited via FACS. Reaction mixtures were reverse transcribed and the barcoded oligos incorporated into the cDNA at 55° C. for 3 minutes, 42° C. for an hour, and 85° C. for 10 minutes. Plates were then frozen at −20° C. overnight.

Sample pooling, library preparation and sequencing. Frozen plates were thawed on ice for sample pooling. RT products from each plate were pooled in two halves (left and right halves of a 96-well plate) and concentrated down using Select-a-Size DNA Clean & Concentrator (Zymo Research, Irvine, Calif.) according to manufacturer's instruction to remove materials shorter than 300 bp. In brief, 500 µL of select-a-size DNA binding buffer was added to 100 µL of cDNA, and mixed by gentle pipetting before centrifugation at 10,000 g for 30 seconds. Columns containing cDNA were washed twice with DNA wash buffer and eluted in 15 uL using DNA Elution Buffer. 1 µL of each sample was used for PCR using Q5 DNA polymerase (New England Biosciences) and 0.2 µM of the primers pltwll_LibPCR_Fw and pltwll_LibPCR_RV. The following PCR thermocycling conditions were used: denaturation at 95° C. for 5 minutes; 10 cycles of the following: 98° C. for 30 seconds, 60° C. for 30 seconds, and 68° C. for 1 minute; and final extension at 68° C. for 5 minutes using Eppendorf Mastercycler Nexus Thermal Cycler (Hauppauge, N.Y.). PCR products were again concentrated down using select-a-Size DNA Clean & Concentrator (Zymo Research, Irvine, Calif.) as described previously to remove products shorter than 300 bp. A 2nd PCR was then conducted using 0.2 µM of the primers pltwell_PCR2_Fw and pltwell_PCR2_Rv. Products with sizes of 300 bp to 1200 bp were size-selected using Pippin Prep DNA Size Selection System (Beverly, Mass.), and sequenced by Illumina MiSeq system (San Diego, Calif.).

Analysis and results. Following MiSeq sequencing of the library, the resulting read pairs from a set of 48 wells were analyzed using a Python script. As a result of the random distribution of barcodes according to a Poisson distribution, 39 of these wells contained at least one wID and at least one wID. Nine (9) wells contained either zero wID barcodes or zero odT barcodes. Using the known structure of the reads (5'-wID-ACGGG-mRNA-BdA16-N8-oDT), oDT BCs were identified from the reverse reads, and the wID BCs from the forward reads. The known sequence of the barcodes was not used in the analysis that follows, demonstrating that this method can determine the sample of origin of nucleic acids without prior knowledge of which barcodes are associated with which sample, and that the data analysis approach is robust to errors introduced by the sequencer.

A set of "dual barcoded transcript reads" was generated from the read pairs for which both an oDT BC and a wID BC were identified. The set consisted of a total of 107,795 read pairs comprising 6,964 distinct barcode pairs. A histogram of frequencies of observed barcode pairs from the dual barcoded transcripts is shown in FIG. 15.

A low level of cross-contamination was expected from the synthesis of the oligos (see IDT DNA Technologies, Reduced Barcode Contamination Using Oligonucleotides With TruGrade™ Processing, Decoded 2(4), 2012). Barcode oligos were synthesized together in sets. With N barcodes synthesized together, if each oligo delivered contains an equal mixture of each of the other N−1 oligos, so that each desired product oligo comprises only a fraction 1−p of the oligo produced, the fraction of reads that will have an expected barcode pair versus pairs arising from contamination can be estimated. The fraction of reads with the expected pair can be estimated as $(1-p)*(1-p)$. The fraction that are contaminants can be estimated as $(1-(1-p)*(1-p))$. If then there are (N−1) different oligo barcodes due to contamination, there are a total of N*N−1 contaminant pairs. The proportion of contaminant pairs can then be estimated as $f=(1-p*p)/\{p*p*(N*N-1)\}$, and the number of read pairs per contaminant for a given number R of reads is PR.

288 total barcodes in plates of 24 at a time were ordered. Conservatively allowing for up to 10% of oligo cross-contamination at the molar level, it was estimated that barcode pairs with fewer than 40 distinct read pairs are likely contamination. Therefore threshold was set, requiring that a given pair of barcodes be observed in a minimum of 50 read pairs for further consideration in our analysis.

Assignment of data to wells and cells. The output reads were assigned to single cells and wells without using prior knowledge of which barcodes were distributed to each well. The starting point of this analysis was the set of 183 pairs of wID BCs and oDT BCs that were supported in the data by at least 50 read pairs. These 183 pairs of BCs were supported by a total of a total of 94,712 read pairs. Each one of these pairs was viewed as an edge (wID BC, oDT BC) in a graph whose vertices were the observed wID BCs and oDT BCs, assigned to edges with at least 50 reads. This graph which represented our data set, was bi-partite with the wID BCs composing one group of nodes, and the oDT BCs composing the other group of nodes. It was noted that cells/wells that had one or more wID BCs and one or more oDT BCs should generate a set of edges that forms a complete bi-partite sub-graph of the graph consisting of all edges in the data (also see FIGS. 13 and 14). Hence, the edges of the graph were assigned to cells/wells by developing an algorithm that decomposed the graph of all the data-set into complete bi-partite graphs.

The steps of the algorithm were as follows:
1. Compute all the connected components of the graph
2. Connected components that were complete bi-partite graphs (bi-cliques) were each assigned to a well/cell

TABLE 3

Results of Analysis.

| Component | Component size | Number wBC | Number odtBC | Number pruned maximal bi-cliques | Number of perfectly reconstructed bi-cliques | Number of partially reconstructed bi-cliques | Number of bi-cliques that intersect 1 well | Number of bi-cliques that intersect 2 wells |
|---|---|---|---|---|---|---|---|---|
| 1 | 48 | 25 | 23 | 12 | 6 | 3 | 0 | 3 |
| 2 | 20 | 12 | 8 | 3 | 3 | 0 | 0 | 0 |
| 3 | 15 | 8 | 7 | 4 | 2 | 1 | 0 | 1 |
| 4 | 11 | 4 | 7 | 2 | 2 | 0 | 0 | 0 |
| 5 | 10 | 2 | 8 | 2 | 1 | 0 | 0 | 1 |
| 6 | 8 | 2 | 6 | 1 | 1 | 0 | 0 | 0 |
| 7 | 6 | 2 | 4 | 1 | 1 | 0 | 0 | 0 |
| 8 | 5 | 2 | 3 | 1 | 1 | 0 | 0 | 0 |
| 9 | 4 | 3 | 1 | 1 | 0 | 0 | 1 | 0 |
| 10 | 4 | 2 | 2 | 1 | 1 | 0 | 0 | 0 |
| 11 | 4 | 2 | 2 | 2 | 1 | 0 | 1 | 0 |
| 12 | 4 | 3 | 1 | 1 | 1 | 0 | 0 | 0 |
| 13 | 2 | 1 | 1 | 1 | 1 | 0 | 0 | 0 |
| 14 | 2 | 1 | 1 | 1 | 1 | 0 | 0 | 0 |
| 15 | 2 | 1 | 1 | 1 | 1 | 0 | 0 | 0 |

3. The other connected components were decomposed into a union of bi-cliques as follows:
a. All bi-cliques that were sub-graphs of the component were determined (algorithm explained below)
b. Out of the set of graphs in 3. a., bi-cliques that were maximal (not included in any other bi-clique) were selected
c. A "pruning" step was applied to remove bi-cliques that were unlikely to be present in the data
Step 3a. of the above algorithm was performed as follows:
1. Sets O and I were generated as follows:
a. For each wID BC in the connected component the set of oDT BCs were determined that were connected to it by an edge, and called it outgoing (wID BC), and then it was added to O both outgoing (wID BC) and all its subsets.
b. In a similar way to a. the set I was generated as follows: for each oDT BC in the connected component the set of wID BCs was determined that were connected to it by an edge and called it incoming (oDT BC), and then it was added to I both incoming (oDT BC) and all its sub sets.
2. Now for each set i in I and each set o in O it was determined if all edges between wID BCs in i and oDT BCs in o were present in the data, and if this was the case bi-cliques were added to the set of all bi-cliques that were sub-graphs of that component
Step 3c. of the above algorithm was performed as follows:
1. With $\lambda=2$ only a fraction 0.0166 of the cells will have more than 5 barcodes of a given type. Hence, any bi-clique constructed by the algorithm that had more than 5 wID BCs or 5 oDT BCs was rejected as a valid construct and was filtered out
2. Cliques that had a single wID BC and 4 or more oDT BC (or vice versa) had a high likelihood of being an ambiguous construct composed of smaller bi-cliques. In view of this ambiguity these bi-cliques were filtered as well.
The heuristics of steps 3b. and 3c. could be replaced by a maximum likelihood approach that decomposes each component into the most likely bi-partite cliques that it comprises, and this would be expected to further improve the results. The likelihood depends on the parameter k, as discussed in our heuristic 3c., and also on the amount of overlap in wID BCs and oDT BCs between the various bi-cliques that make up the component.

Table 2 shows that the data from the 39 wells that contributed to this data set generated 15 components (note that only 39 of the 48 wells had both wID and odT BCs. 9 wells had only wID barcodes or only odT barcodes and thus could not yield barcode pairs). The number of wID BCs and oDT BCs and the number of pruned maximal bi-cliques that resulted from the decomposition algorithm is presented. In addition, Table 2 presents the numbers of bi-cliques that were exact matches to an expected clique, that were a proper subset of an expected bi-clique, or that intersected with either one or two expected graphs.

34 complete bipartite graphs were generated out of 15 connected components. Out of these 34, 23 were perfect matches to an expected graph. An additional 4 graphs were proper subsets of an expected graph. Hence 23/34=67% of resulting cliques were perfectly generated, and 27/34=79% were at least partially reconstructed, and had no erroneous edges assigned to them. Overall 27/48=56% of the wells included in the experiment were successfully assigned associated barcodes and mRNA. These successful reconstructions were possible despite the presence in the data set of spurious read pairs due to cross-contamination during barcode oligo manufacturing, which could be filtered out in the data processing.

This multi-barcoding scheme greatly outperforms a mono-barcoding scheme in which the goal is to assign a single barcode to each cell. In a mono-barcoding scheme with Poisson loading, using $\lambda=0.1$ or less would be a natural choice (see Macosko et al., Cell, 161:5 (2015), which uses a lambda of 0.06). With $\lambda=0.1$, approximately 90.4% of cells would receive no barcode, approximately 9.0% would receive exactly one barcode, and approximately 0.5% would receive more than one barcode. In the experiment described here, 56%/(100−90.4)% equals 5.8 times as many cells as would have been successfully analyzed using a mono-barcoding scheme.

What is claimed is:

1. A method of identifying the origin of a nucleic acid sample comprising the steps of
   (a) forming a plurality of reaction mixtures, each comprising a nucleic acid sample comprising mRNA transcripts from a single cell and a set of barcodes, each attached to a solid surface, comprising one or more 5' nucleic acid constructs each comprising a unique 5' barcode and one or more 3' nucleic acid constructs each comprising a unique 3' barcode;
      wherein the one or more 3' nucleic acid constructs each comprises a unique molecular identifier sequence (UMI), a barcode sequence, and a poly T sequence, wherein the poly T sequence anneals to a poly A tail of the 3' end of an mRNA transcript in the nucleic acid sample,
      wherein the one or more 5' nucleic acid constructs each comprises a barcode sequence and a binding sequence,
   (b) cleaving from the solid surface (i) the one or more unique 5' barcodes, (ii) the one or more unique 3' barcodes, or (iii) both the one or more unique 5' barcodes and the one or more unique 3' barcodes;
   (c) incorporating the set of barcodes into the nucleic acid molecules of the sample by reverse transcription of the mRNA transcripts using a reverse transcriptase, wherein, for each mRNA transcript, the reverse transcriptase
      (i) reverse-transcribes the mRNA transcript to produce a single cDNA nucleic acid molecule that includes both the 3' barcode and a sequence complementary to the mRNA sequence;
      (ii) upon reaching the end of the mRNA transcript, adds nucleotides complementary to and anneals to the binding sequence on the 5' nucleic acid construct; and
      (iii) undergoes template-switching to continue the reverse transcription to incorporate the 5' barcode into the same single cDNA nucleic acid molecule, thereby producing the nucleic acid molecules incorporated with the set of barcodes; and
   (d) identifying the set of barcodes incorporated into the nucleic acid molecules of the single cell thereby identifying the cell origin of the nucleic acid sample, wherein the combination of the one or more unique 5' and 3' barcodes in the nucleic acid sample identifies the cell origin of the nucleic acid sample.

2. The method of claim 1, wherein forming the reaction mixture comprises contacting the single cell with the set of barcodes and lysing the cell to provide the nucleic acid sample from the single cell.

3. The method of claim 1, wherein forming the reaction mixture comprises providing cells in a suspension buffer and contacting the suspension buffer comprising the cells with a barcoding buffer comprising the set of barcodes under conditions to form the reaction mixture comprising the single cell and the set of barcodes.

4. The method of claim 1, wherein forming the reaction mixture comprises providing a cell in a suspension buffer, and contacting the suspension buffer with a barcoding buffer comprising the 5' and 3' nucleic acid constructs under conditions to form the reaction mixture comprising the single cell and at least one 5' nucleic acid construct and at least one 3' nucleic acid construct.

5. The method of claim 1, wherein forming the reaction mixture comprises providing a cell in a suspension buffer, and contacting the suspension buffer with a first barcoding buffer comprising the 5' nucleic acid constructs and a second barcoding buffer comprising the 3' nucleic acid constructs under conditions to form the reaction mixture comprising the single cell and at least one 5' nucleic acid construct and at least one 3' nucleic acid construct.

6. The method of claim 1, wherein each 5' nucleic acid construct is provided in multiple copies attached to the solid surface.

7. The method of claim 1, wherein each 3' nucleic acid construct is provided in multiple copies attached to the solid surface.

8. The method of claim 6, wherein the solid surface is a bead, microbead, microparticle, microsphere, nanoparticle, nanobead, or hydrogel.

9. The method of claim 1, wherein the reaction mixture comprises the nucleic acid sample from the single cell, at least one bead comprising multiple copies of the 5' nucleic acid constructs, and at least one bead comprising multiple copies of the 3' nucleic acid construct.

10. The method of claim 1, wherein each 5' and 3' nucleic acid construct further comprises a photocleavable linker or a restriction enzyme site.

11. The method of claim 1, wherein each 5' nucleic acid construct further comprises a photocleavable linker and each 3' nucleic acid construct further comprises a restriction enzyme site.

12. The method of claim 1, wherein each 5' nucleic acid construct further comprises a restriction enzyme site and each 3' nucleic acid construct further comprises a photocleavable linker.

13. The method of claim 11, wherein the method further comprises contacting the reaction mixture with a restriction enzyme and exposing the reaction mixture to UV light to release the 5' and 3' nucleic acid constructs from the solid surface.

14. The method of claim 10, wherein the 5' and 3' nucleic acid constructs further comprise a restriction enzyme site and the method further comprises contacting the reaction mixture with a restriction enzyme to release the 5' and 3' nucleic acid constructs from the solid surface.

15. The method of claim 10, wherein the 5' and 3' nucleic acid constructs further comprise a photocleavable linker and the method further comprises exposing the reaction mixture to UV light to release the 5' and 3' nucleic acid constructs from the solid surface.

16. The method of claim 1, wherein the 5' nucleic acid construct is a double stranded nucleic acid construct comprising a promoter and wherein the 5' nucleic acid construct serves as a template to produce multiple copies of the 5' nucleic acid construct.

17. The method of claim 1, wherein the set of barcodes comprises 2, 3, 4, 5, 6, 7, or 8 5' nucleic acid constructs and 2, 3, 4, 5, 6, 7, or 8 3' nucleic acid constructs.

18. The method of claim 1, wherein the 3' nucleic acid constructs further comprise a binding sequence.

19. The method of claim 18, wherein the binding sequence comprises a poly-T sequence.

20. The method of claim 19, wherein the poly-T sequence binds to the poly-A sequences on the nucleic acid molecules of the sample.

21. The method of claim 1, wherein the barcodes on the 3' nucleic acid constructs are incorporated by reverse transcription.

22. The method of claim 21, wherein the reverse transcription produces nucleic acid molecules comprising the 3' barcode.

23. The method of claim 22, wherein the reverse transcriptase enzyme adds two to five cytosine residues to the end of the nucleic acid molecules in the sample.

24. The method of claim 23, wherein the two to five cytosine residues provide provides a binding sequence complementary to a binding sequence on the 5' nucleic acid constructs.

25. The method of claim 24, wherein the binding sequence on the 5' nucleic acid constructs comprises a poly-G sequence.

26. The method of claim 25, wherein the binding sequence on the 5' nucleic acid constructs binds to poly-C sequences on the nucleic acid molecules of the sample.

27. The method of claim 1, wherein the 5' nucleic acid construct is incorporated into the nucleic acid sample using a reverse transcriptase enzyme.

28. The method of claim 21, wherein the reverse transcriptase is an M-MLV enzyme.

29. The method of claim 28, wherein the reverse transcriptase is MMLV H-reverse transcriptase.

30. The method of claim 1, wherein the nucleic acid sample is further amplified to produce multiple copies of the plurality of nucleic acid sequences each sequence comprising a 5' barcode and a 3' barcode.

31. The method of claim 1, wherein the nucleic acid molecules comprise mRNAs.

32. The method of claim 31, wherein the mRNAs comprise at least 1, 3, 10, 30, 100, 300, 1,000, 3,000, 10,000, 30,000, 100,000, 300,000, or 1,000,000 mRNAs.

33. The method of claim 1, wherein the barcodes in the nucleic acid sample are identified by sequencing.

34. The method of claim 1, wherein the set of barcodes comprises at least two 5' nucleic acid constructs each construct comprising a unique 5' barcode.

35. The method of claim 1, wherein the set of barcodes comprises at least two 3' nucleic acid constructs each construct comprising a unique 3' barcode.

36. The method of claim 1, wherein one or more of the nucleic acid molecules comprises two or more unique barcodes.

37. The method of claim 36, wherein the unique barcodes are located at the 5' end, the '3' end or both the 5' and 3' end of the nucleic acid molecules.

38. The method of claim 1, wherein forming the plurality of reaction mixtures comprises adding the set of barcodes to the plurality of reaction mixtures at a lambda greater than 0.5, 0.6, 0.7, 0.8, 0.9, 1.0, 2.0, 3.0, 4.0 or 5.0.

39. The method of claim 1, wherein the reaction mixture is a droplet.

40. The method of claim 1, wherein the one or more unique barcodes are present in 30%, 40%, 50%, 60%, 70%, 80%, 90% or 100% of the reaction mixtures.

* * * * *

SEQUENCE LISTING

<160> NUMBER OF SEQ ID NOS: 6

<210> SEQ ID NO 1
<211> LENGTH: 51
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (27)..(34)
<223> OTHER INFORMATION: n is a, c, g, or t

<400> SEQUENCE: 1
ggctcggaga tgtgtataag agacagnnnn nnnntttttt tttttttttt v        51

<210> SEQ ID NO 2
<211> LENGTH: 30
<212> TYPE: DNA
<213> ORGANISM: artificial sequence
<220> FEATURE:
<223> OTHER INFORMATION: synthetic construct

<400> SEQUENCE: 2
ggaagatagg gataacaggg taatgacggg                                30

<210> SEQ ID NO 3
<211> LENGTH: 65
<212> TYPE: DNA
<213> ORGANISM: artificial sequence
<220> FEATURE:
<223> OTHER INFORMATION: synthetic construct

<400> SEQUENCE: 3
aatgatacgg cgaccaccga gatctacact cgtcggcagc ggaagatagg gataacaggg    60
taatg                                                                65

<210> SEQ ID NO 4
<211> LENGTH: 55
<212> TYPE: DNA
<213> ORGANISM: artificial sequence
<220> FEATURE:
<223> OTHER INFORMATION: synthetic construct

<400> SEQUENCE: 4
caagcagaag acggcatacg agatgtctcg tgggctcgga gatgtgtata agaga     55

<210> SEQ ID NO 5
<211> LENGTH: 17
<212> TYPE: DNA
<213> ORGANISM: artificial sequence
<220> FEATURE:
<223> OTHER INFORMATION: synthetic construct

```
<400> SEQUENCE: 5
aatgatacgg cgaccac                                                      17

<210> SEQ ID NO 6
<211> LENGTH: 19
<212> TYPE: DNA
<213> ORGANISM: artificial sequence
<220> FEATURE:
<223> OTHER INFORMATION: synthetic construct

<400> SEQUENCE: 6
caagcagaag acggcatac                                                    19
```